United States Patent
Tsuji et al.

(10) Patent No.: US 10,988,518 B2
(45) Date of Patent: Apr. 27, 2021

(54) **METHOD FOR EFFICIENTLY PRODUCING β MYOSIN HEAVY CHAIN IN CARDIAC MUSCLE CELLS DIFFERENTIATED FROM INDUCED PLURIPOTENT STEM CELLS DERIVED FROM *HOMO SAPIENS***

(71) Applicant: Panasonic Corporation, Osaka (JP)

(72) Inventors: Kiyotaka Tsuji, Osaka (JP); Li Liu, Kyoto (JP)

(73) Assignee: PANASONIC CORPORATION, Osaka (JP)

( * ) Notice: Subject to any disclaimer, the term of this patent is extended or adjusted under 35 U.S.C. 154(b) by 553 days.

(21) Appl. No.: 15/848,020

(22) Filed: Dec. 20, 2017

(65) Prior Publication Data
US 2018/0251504 A1    Sep. 6, 2018

(30) Foreign Application Priority Data
Mar. 3, 2017    (JP) .............................. JP2017-039998

(51) Int. Cl.
| | |
|---|---|
| *C12N 5/00* | (2006.01) |
| *C12N 5/071* | (2010.01) |
| *C12P 21/06* | (2006.01) |
| *C07K 14/47* | (2006.01) |
| *C12M 1/42* | (2006.01) |
| *C12N 13/00* | (2006.01) |
| *C12P 21/00* | (2006.01) |
| *C12P 21/02* | (2006.01) |
| *C12N 5/0735* | (2010.01) |

(52) U.S. Cl.
CPC ......... *C07K 14/4716* (2013.01); *C12M 35/02* (2013.01); *C12N 13/00* (2013.01); *C12P 21/00* (2013.01); *C12P 21/02* (2013.01); *C12N 5/0606* (2013.01); *C12N 5/069* (2013.01)

(58) Field of Classification Search
CPC ...... C12N 5/0606; C12N 6/069; C12N 13/00; C12M 35/02
USPC ............................... 435/366, 375, 68.1, 69.1
See application file for complete search history.

(56) References Cited

U.S. PATENT DOCUMENTS

| | | |
|---|---|---|
| 6,132,683 A | 10/2000 | Sugihara et al. |
| 8,916,189 B2 | 12/2014 | Watanabe et al. |
| 2015/0017718 A1 | 1/2015 | Nakatsuji et al. |
| 2016/0083715 A1 | 3/2016 | Rasmusson et al. |
| 2017/0349883 A1 | 12/2017 | Yoshida et al. |

FOREIGN PATENT DOCUMENTS

| | | |
|---|---|---|
| EP | 3208328 | 8/2017 |
| JP | 60-110287 | 6/1985 |
| JP | 4-141087 | 5/1992 |
| JP | 11-187865 | 7/1999 |
| JP | 2004-105148 A | 4/2004 |
| JP | 2013-188173 | 9/2013 |
| JP | 2016-518853 A | 6/2016 |
| WO | 2016/060260 | 4/2016 |
| WO | 2016/104614 A1 | 6/2016 |

OTHER PUBLICATIONS

Stoppel, W. et al., "Electrical and mechanical stimulation of cardiac cells and tissue constructs." Advanced Drug Delivery Reviews; 2016, Jan. 15; vol. 96; pp. 135-55.
Nunes, S. et al. "Bioware: a new platform for maturation of human pluripotent stem cell derived cardiomyocytes," Nature Methods; Aug. 2013; vol. 10; No. 8; pp. 781-787, Supplementary Materials.

*Primary Examiner* — Shin Lin Chen
(74) *Attorney, Agent, or Firm* — McDermott Will and Emery LLP

(57) ABSTRACT

The present invention provides a method for producing a β myosin heavy chain in cardiac muscle cells differentiated from induced pluripotent stem cells derived from Homo sapiens. In the present method, first, a liquid culture medium containing the cardiac muscle cells is supplied onto a substrate comprising a first electrode, a second electrode and insulative fibers on the surface thereof. At least a part of the insulative fibers is located between the first electrode and the second electrode in a top view of the substrate. Then, the substrate is left at rest. Finally, the cardiac muscle cells are cultivated, while a pulse electric current is applied to the cardiac muscle cells through the first electrode and the second electrode.

6 Claims, 16 Drawing Sheets
Specification includes a Sequence Listing.

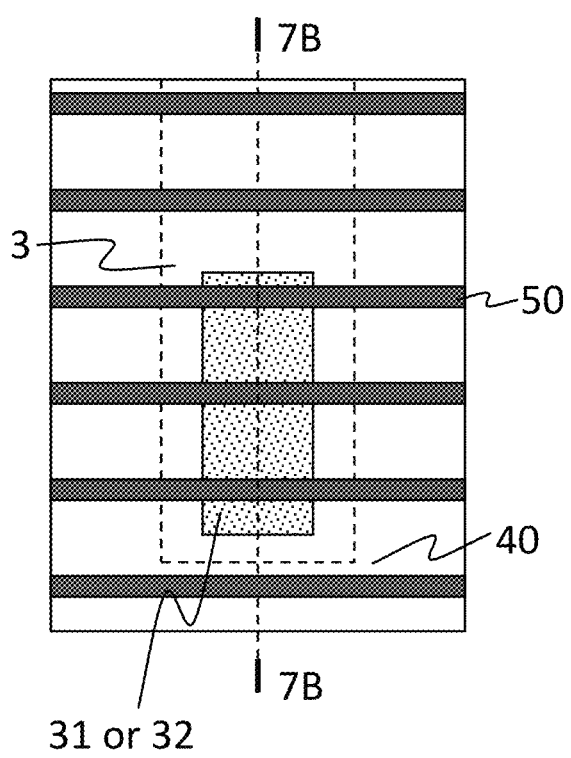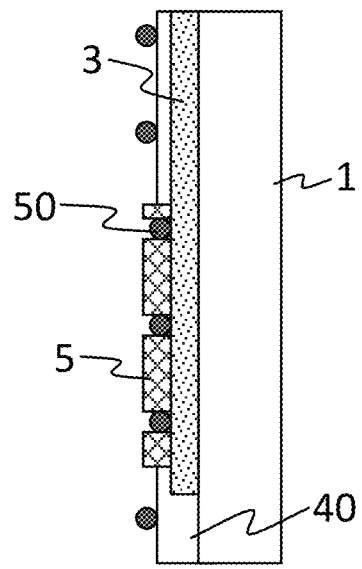
FIG. 7A
FIG. 7B

Nano Fiber Direction

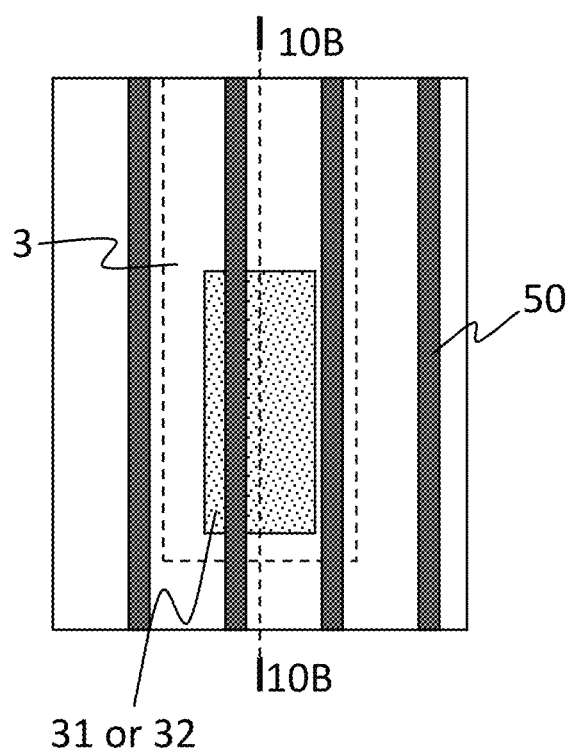
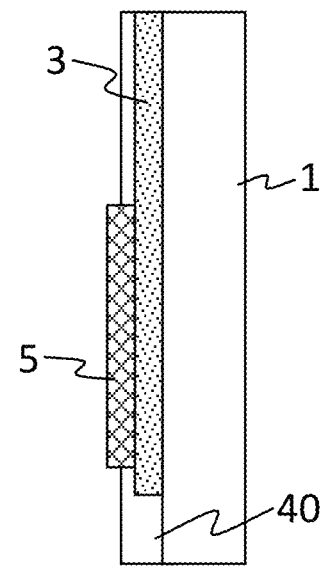
FIG. 10A
FIG. 10B 31 or 32

METHOD FOR EFFICIENTLY PRODUCING β MYOSIN HEAVY CHAIN IN CARDIAC MUSCLE CELLS DIFFERENTIATED FROM INDUCED PLURIPOTENT STEM CELLS DERIVED FROM *HOMO SAPIENS*

INCORPORATION BY REFERENCE-SEQUENCE LISTING

The material contained in the ASCII text file named "P1006798US01_ST25.txt" created on Nov. 22, 2017, and having a file size of 18,746 bytes is incorporated by reference herein.

BACKGROUND

1. Technical Field

The present invention relates to a method for efficiently producing a β myosin heavy chain in cardiac muscle cells differentiated from induced plluripotent stem cells derived from Homo sapiens.

2. Description of the Related Art

Japanese patent application laid-open publication No. Sho 60-110287 discloses that cell proliferation is promoted by application of electric pulse to the cultivated cells.

Japanese patent application laid-open publication No. Hei 4-141087 discloses a method that cells are differentiated by application of electric voltage to the cells through a liquid culture medium.

U.S. Pat. No. 8,916,189 discloses a cell culture support for forming string-shaped cardiomyocyte aggregates.

Japanese patent application laid-open publication No. 2013-188173 discloses a method for creating cell tissue having function.

U.S. Patent Application Publication No. 2015/0017718 discloses a method for inducing cardiac differentiation of a pluripotent stem cell.

WO 2016/060260 discloses a method for producing a tissue fragment, particularly a myocardial tissue fragment which contains cultured cells having an oriented configuration. See FIG. 4B, FIG. 9A, and paragraphs 0055, 0131, 0141, 0142, and 0153 thereof.

SUMMARY

The present invention provides a method for producing a β myosin heavy chain in cardiac muscle cells differentiated from induced pluripotent stem cells derived from Homo sapiens, the method comprising:
(a) supplying a liquid culture medium containing the cardiac muscle cells onto a substrate comprising a first electrode, a second electrode and insulative fibers on the surface thereof to coat a surface of the first electrode, a surface of the second electrode, and an region between the first electrode and the second electrode with the cardiac muscle cells;
wherein
at least apart of the insulative fibers is located between the first electrode and the second electrode in a top view of the substrate; and
an angle formed between each of not less than 90% of the insulative fibers and an imaginary straight line which passes through both the first electrode and the second electrode is not more than ±20 degrees in the top view;
(b) leaving the substrate at rest; and
(c) cultivating the cardiac muscle cells, while a pulse electric current is applied to the cardiac muscle cells through the first electrode and the second electrode.

The present invention provides a method for efficiently producing a β myosin heavy chain in cardiac muscle cells differentiated from induced pluripotent stem cells derived from Homo sapiens.

BRIEF DESCRIPTION OF THE DRAWINGS

FIG. 7A shows an enlarged top view of the end part of the electric wiring.

FIG. 7B shows a cross-sectional view taken along the line 7B-7B included in FIG. 7A.

FIG. 10A shows an enlarged top view of the end part of the electric wiring in the comparative examples 2 and 3.

FIG. 10B shows a cross-sectional view taken along the line 10B-10B included in FIG. 10A.

DETAILED DESCRIPTION OF THE EMBODIMENT

Figure 1:
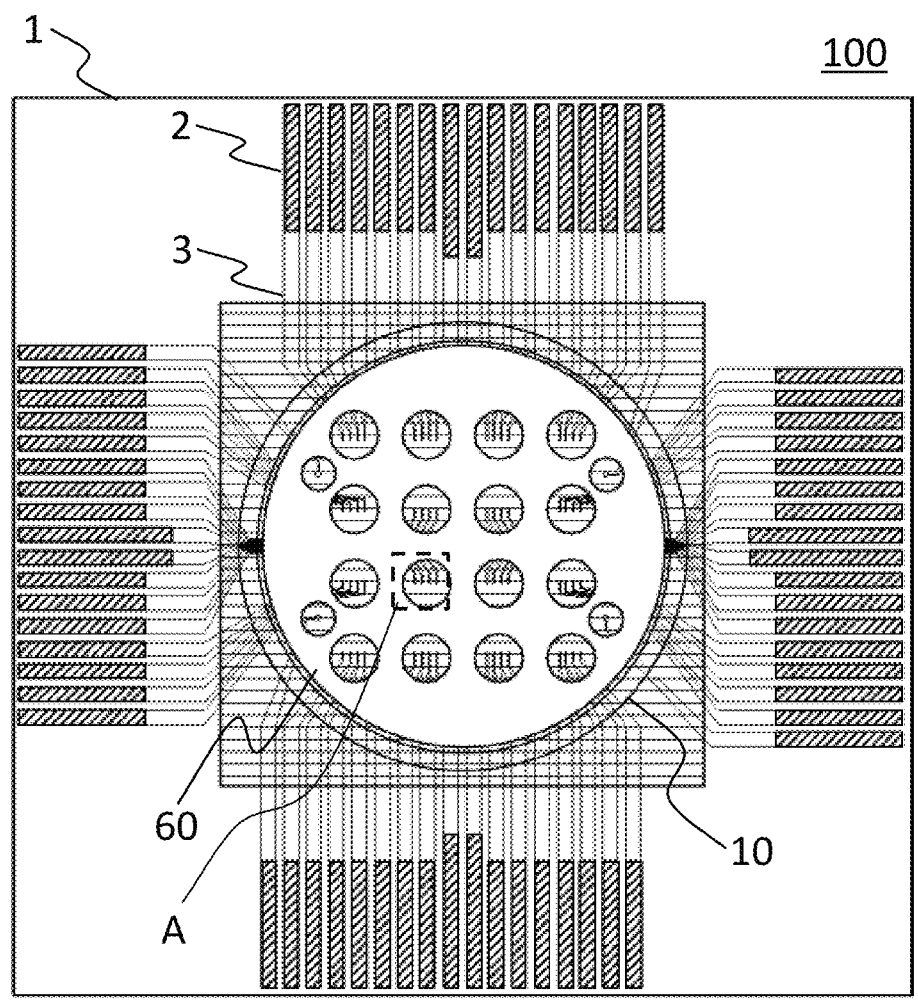
FIG. 1 shows a top view of a substrate.

Hereinafter, an embodiment of the present invention will be described with reference to the drawings.

As disclosed in FIG. 2C of U.S. Patent Application Publication No. 2015/0017718, an amount of production of a β myosin heavy chain (hereinafter, referred to as "β MHC") is significantly smaller in cardiac muscle cells differentiated from induced pluripotent stem cells derived from Homo sapiens than in cardiac muscle cells included in a living body. The β MHC is one kind of polypeptides providing support for a structure of the cell. For the maturation of the cardiac muscle cells differentiated from induced pluripotent stem cells derived from Homo sapiens, it is important to produce the β MHC efficiently.

The β MHC has a primary structure consisting of the amino acid sequence represented by the following SEQ ID NO: 1.

MGDSEMAVFGAAAPYLRKSEKERLEA-QTRPFDLKKDVFVPDDKQEFVKAKIVS-REGGKVTAETEYGKTVT VKEDQVMQQNPPKFDKIEDMAMLTFLHEP-AVLYNLKDRYGSWMIY-TYSGLFCVTVNPYKWLPVYTPEVVA AYRGKKRSEAPPHIFSISDNAYQYMLT-DRENQSILITGESGAGKTVNTKRVIQYFAVI-AAIGDRSKKDQS PGKGTLEDQIIQANPALEAFG-NAKTVRNDNSSRFGKFIRIHFGATGKLASADIE TYLLEKSRVIFQLKAE RDYHIFYQILSNKKPELL-DMLLITNNPYDYAFISQGETTVASIDDAEEL-MATDNAFDVLGFTSEEKNSMY KLT-GAIMHFGNMKFKLKQREEQAEPDGTEEADK SAYLMGLNSADLLKGLCH-PRVKVGNEYVTKGQNV QQV IYATGALAKAVYERMFNWMVTRI-NATLETKQPRQYFIGVLDIAGFEIFDFNS-FEQLCINFTNEKLQQFFN HHMFVLEQEEYKK-EGIEWTFIDEGMDLQACIDLIEKPMGIMSILEEE CMFPKATDMTFKAKLFDNHLGKS ANFQKPRNIKGKPEAHFSLIHYAGIV-DYNIIGWLQKNKDPLNETVVGLYQKSSLKLL-STLFANYAGADAP IEKGKGKAKKGSSFQTVSALHRENLNKLMTNL RSTHPHFVRCIIPNETKSPGVMDNPLVMHQLRC-NGVLE GIRICRKGFPNRILYGDFRQRYRILN-PAAIPEGQFIDSRKGAEKLLSSL-DIDHNQYKFGHTKVFFKAGLL GLLEEMRDERLSRIITRIQAQSRGV-LARMEYKKLLERRDSLLVIQWNI-RAFMGVKNWPWMKLYFKIKPLL KSAEREKE-MASMKEEFTRLKEALEKSEARRKELEEKMVSL LQEKNDLQLQVQAEQDNLADAEERCDQLIK NKIQLEAKVKEMNERLEDEEEMNAEL-TAKKRKLEDECSELKRDIDDLELT-LAKVEKEKHATENKVKNLTE EMAGLDEIIAK-LTKEKKALQEAHQQALDDLQAEEDKVNTLTK AKVKLEQQVDDLEGSLEQEKKVRMDLER AKRKLEGDLKLTQESIMDLENDKQQLDER-LKKKDFELNALNARIEDEQAL-GSQLQKKLKELQARIEELEE ELESERT-ARAKVEKLRSDLSRELEEISERLEEAGGATSVQ IEMNKKREAEFQKMRRDLEEATLQHEATAA ALRKKHADSVAEL-GEQIDNLQRVKQKLEKEKSEFKLELDDVTSN-MEQIIKAKANLEKMCRTLEDQMNEHR SKAEETQRSVNDLTSQRAKLQTENGELSRQLDE-KEALISQL-TRGKLTYTQQLEDLKRQLEEEVKAKNALA HALQSARHDCDLLREQYEEETEAKAELQRVLS-KANSEVAQWRTKYETDAIQRTEELEE-AKKKLAQRLQEA EEAVEAVNAKCSSLEKTKHRLQNEIEDLMVD-VERSNAAAAALDKKQRNFDKILAEWKQKY-EESQSELESS QKEARSLSTELFKLKNAYEE-SLEHLETFKRENKNLQEEISDLTEQLGSSGKTIH ELEKVRKQLEAEKMEL QSALEEAEASLEHEEG-KILRAQLEFNQIKAEIERK-LAEKDEEMEQAKRNHLRVVDSLQTSLDAE-TRSRNE ALRVKKKMEGDLNEMEIQLSHANRMAAEA-QKQVKSLQSLLKDTQIQLDDAVRANDDLKEN-IAIVERRNNL LQAELEELRAVVEQTERSRK-LAEQELIETSERVQLLHSQNTSLINQKKKMDA DLSQLQTEVEEAVQECRN AEEKAKKAITDAAM-MAEELKKEQDTSAHLERMKKNMEQ-TIKDLQHRLDEAEQIALKGGKKQLQKLEARVR ELENELEAEQKRNAESVKGMRKSERRIKELTYQ-TEEDRKNLLRLQDLVDKLQLKVKAYKRQAEE-AEEQAN TNLSKFRKVQHELDEAEERADI-AESQVNKLRAKSRDIGTKGLNEE (SEQ ID NO: 1)

For reference, myosin regulatory light chain 2 (hereinafter, referred to as "MYL2") is also produced in the cardiac muscle cells. The MYL2 has a primary structure consisting of the amino acid sequences represented by the following SEQ ID NO: 2.

MAPKKAKKRAGGANSNVFSMFEQTQIQEFKEAF-TIMDQNRDGFIDKNDLRDTFAALGRVNVKN EEI-DEMIKEAPGPINFTVFLTMFGEKLK-GADPEETILNAFKVFDPEGKGVLKADYVREMLTTQ AERFSKE EVDQMFAAFPPDVTGNLDYKNLVHIITH-GEEKD (SEQ ID NO: 2)

Hereinafter, the cardiac muscle cells differentiated from induced pluripotent stem cells derived from Homo sapiens are just referred to as "cardiac muscle cells". As well known, the induced pluripotent stem cells may be referred to as "iPS cells".

(Step (a))

First, a liquid culture medium containing cardiac muscle cells are supplied on a substrate 100 comprising a first electrode, a second electrode, and insulative fibers on the surface thereof.

Figure 2:
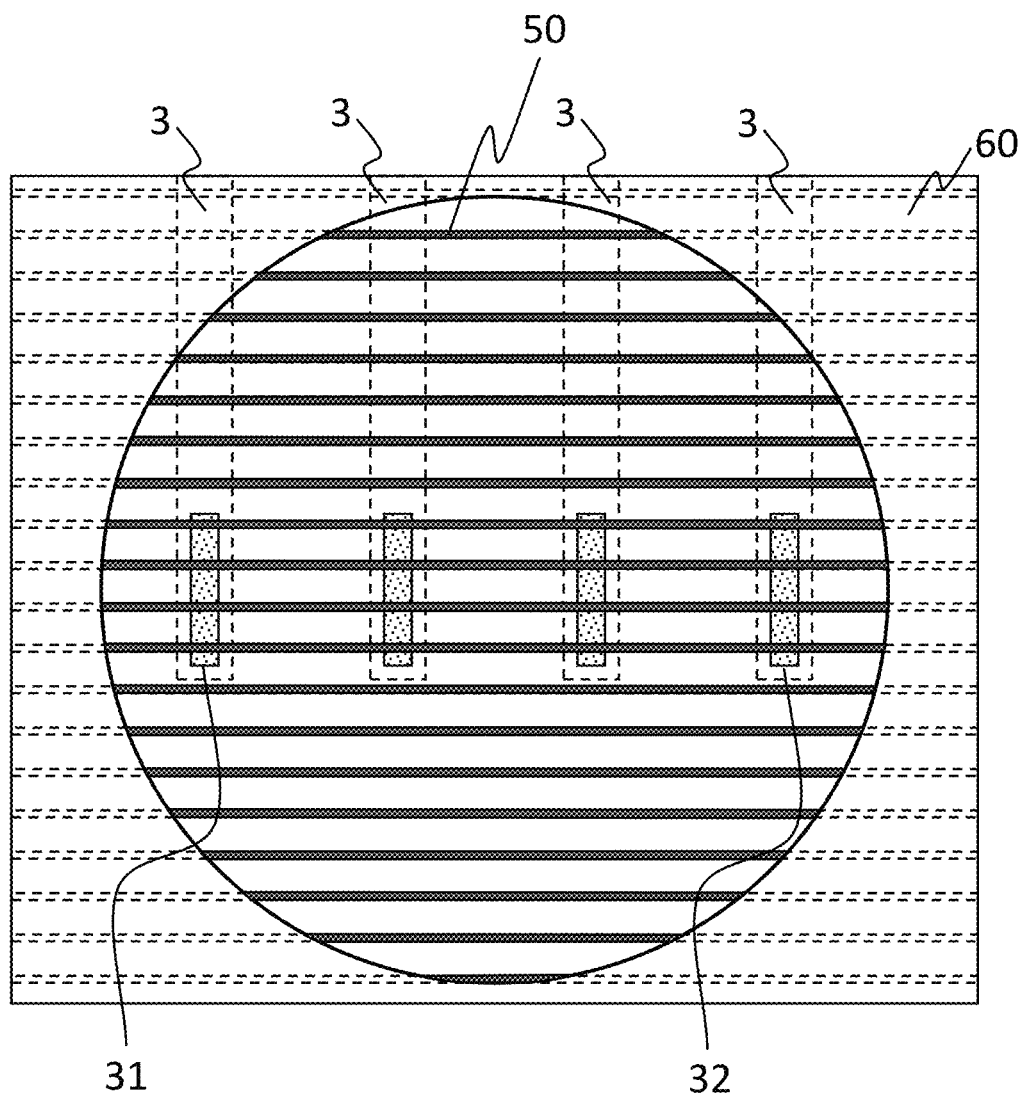
FIG. 2 shows an enlarged view of a region A included in FIG. 1.

FIG. 1 shows a top view of the substrate 100. FIG. 2 shows an enlarged view of a region A included in FIG. 1.

As shown in FIG. 1, the substrate 100 comprises a glass base 1 and an enclosure 10 located on the glass base 1. The surface of the glass base 1 is provided with electric contacts 2 and electric wirings 3. Each of the electric contacts 2 is connected to one end of one electric wiring 3. Within the enclosure 10, an insulative sheet 60 is disposed on the glass base 1. The electric wirings 3 are covered with the insulative sheet 60.

As shown in FIG. 2, other ends of the electric wirings 3 are exposed. The exposed parts function as a first electrode 31 and a second electrode 32. In FIG. 2, four electric wirings 3 are drawn. The first electrode 31 is formed of the exposed end part of the electric wiring 3 located on the left. Similarly, the second electrode 32 is formed of the exposed end part of the electric wiring 3 located on the right.

As shown in FIG. 1 and FIG. 2, insulative fibers 50 are disposed on the surface of substrate 100. The fibers 50 are required to be insulative. This is because a short circuit is prevented from being formed erroneously between the first electrode 31 and the second electrode 32. In case where the short circuit is formed erroneously, a pulse electric current which will be described later fails to be applied to the cardiac muscle cells.

As shown in FIG. 2, at least a part of the insulative fibers 50 is located between the first electrode 31 and the second electrode 32. In case where the insulative fibers 50 are not located between the first electrode 31 and the second electrode 32 (including a case where no insulative fibers 50 are provided on the substrate 100), the β MHC is not produced efficiently, as demonstrated in the comparative example 6 which will be described later.

The insulative fibers 50 are exposed on the surface of the substrate 100. The first electrode 31 and the second electrode 32 are also exposed on the surface of substrate 100.

The insulative fibers 50 have orientation such that an angle formed between each of not less than 90% of the insulative fibers 50 and an imaginary straight line which passes through both the first electrode 31 and the second electrode 32 is not more than ±20 degrees in the top view of substrate 100. In other words, each of the not less than 90% of the insulative fibers 50 forms an angle of not more than 20 degrees with regard to the imaginary straight line. Therefore, not less than 90% of the insulative fibers 50 are substantially parallel to a direction of an electric field generated when an electric current (e.g., pulse electric current) is caused to flow between the first electrode 31 and the second electrode 32. Needless to say, the imaginary straight line does not exist actually on the substrate 100. Desirably, the angle is not more than ±5 degrees. See the paragraph 0023 of U.S. patent application Ser. No. 15/519,341, which is incorporated herein by reference.

In case where less than 90% of the insulative fibers 50 are substantially parallel to the imaginary straight line which passes through both the first electrode 31 and the second electrode 32, the β MHC is not produced efficiently. See the comparative examples 3-6 which will be described later. In the comparative examples 2-3, almost all of the insulative fibers 50 are substantially perpendicular to the imaginary straight line which passes through both the first electrode 31 and the second electrode 32. In other words, in the comparative examples 2-3, each of the almost all of the insulative fibers 50 forms an angle of approximately 90 degrees with regard to the imaginary straight line. In the comparative examples 4-5, a roughly half of the insulative fibers 50 are perpendicular to the imaginary straight line which passes through both the first electrode 31 and the second electrode 32, and the other roughly half of the insulative fibers 50 are parallel to the imaginary straight line.

Desirably, each of the insulative fibers 50 has a diameter of not less than 1 micrometer and not more than 5 micrometers. It is desirable that the material of the insulative fibers 50 is selected from the group consisting of polystyrene, polycarbonate, polymethylmethacrylate, polyvinyl chloride, polyethylene terephthalate, polyamide, polymethylglutarimide, or polylactic acid. It is desirable that the distance between the first electrode 31 and the second electrode 32 is not less than 150 micrometers and not more than 5,000 micrometers.

One example of a fabrication method of the substrate 100 will be described in more detail in the examples which will be described later. A skilled person who has read the examples which will be described later would understand easily the fabrication method of the substrate 100.

Figure 8A:
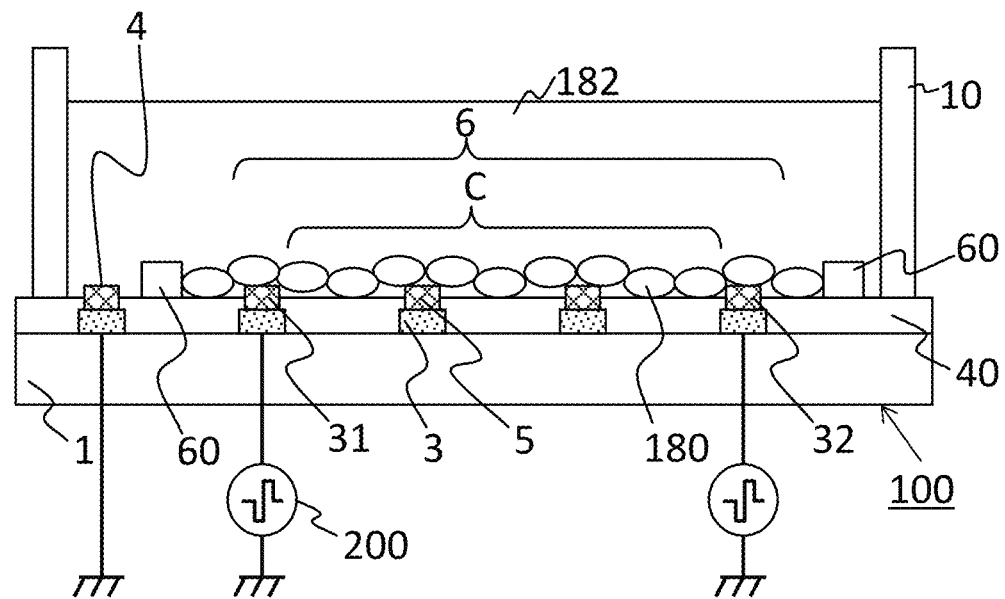
FIG. 8A shows a cross-sectional view of the substrate on which a liquid culture medium has been supplied.

As shown in FIG. 8A, a liquid culture medium 182 containing cardiac muscle cells 180 is supplied to the surface of the above-mentioned substrate 100. The liquid culture medium 182 is spread onto the surface of the substrate 100 within the enclosure 10. In this way, the surface of the first electrode 31, the surface of the second electrode 32, and a region C between the first electrode 31 and the second electrode 32 are coated with the cardiac muscle cells. In case where at least one of the surface of the first electrode 31, the surface of the second electrode 32, and the region C fails to be coated with the cardiac muscle cells, the pulse electric current fails to be applied to the cardiac muscle cells 180 in the step (b) which will be described later. As a result, the β MHC fails to be produced efficiently. As just described, in the step (a), the liquid culture medium 182 containing the cardiac muscle cells 180 having an amount sufficient to coat the surface of the first electrode 31, the surface of the second electrode 32, and the region C is supplied to the surface of substrate 100.

(Step (b))

The Step (b) is conducted out after the step (a). In the Step (b), the substrate 100 is left at rest. In this way, the cardiac muscle cells adhere on the insulative fibers 50 or the surface of substrate 100. Desirably, the substrate 100 is left at rest over 24 hours.

(Step (c))

Figure 8B:
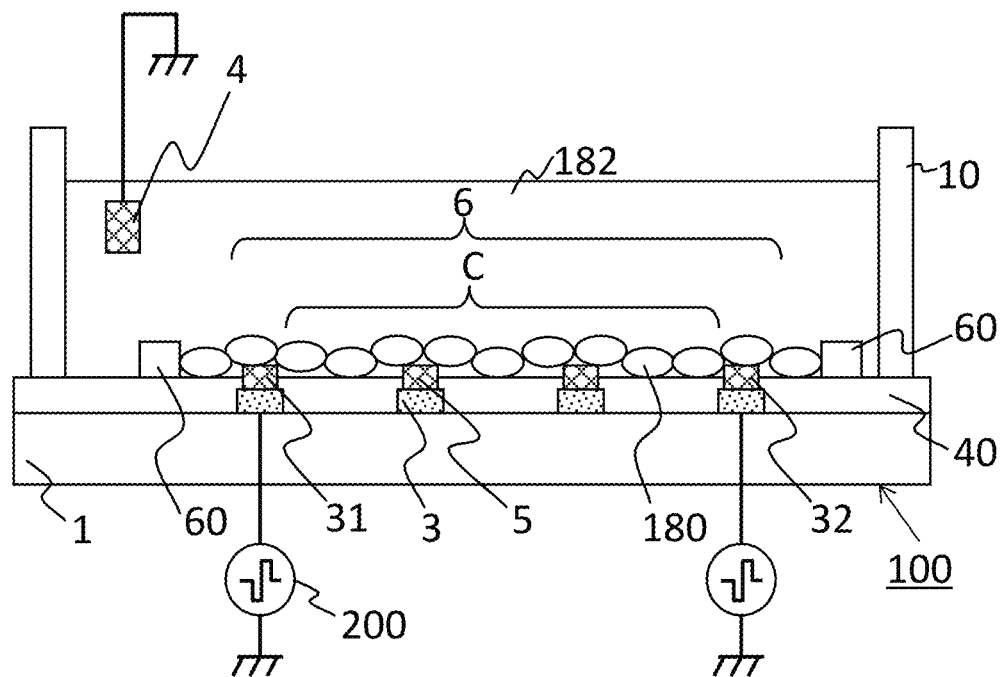
FIG. 8B shows a cross-sectional view of the substrate on which a liquid culture medium has been supplied.

The Step (c) is conducted after the step (b). In the step (c), while a pulse electric current is applied to the cardiac muscle cells 180 through the first electrode 31 and the second electrode 32, the cardiac muscle cells 180 are cultivated. The same pulse electric current may be applied to the first electrode 31 and the second electrode 32. When the pulse electric current is applied to the first electrode 31 and the second electrode 32, a reference electrode 4 may be used. The reference electrode 4 is grounded. As shown in FIG. 8A, the reference electrode 4 may be provided on the surface of the substrate 100. However, as shown in FIG. 8B, the reference electrode 4 is not necessary to be provided on the surface of the substrate 100. In FIG. 8B, the reference electrode 4 is included in the inside of the liquid culture medium 182. Anyway, it is desirable that the reference electrode 4 is in contact with the liquid culture medium 182.

Figure 3:
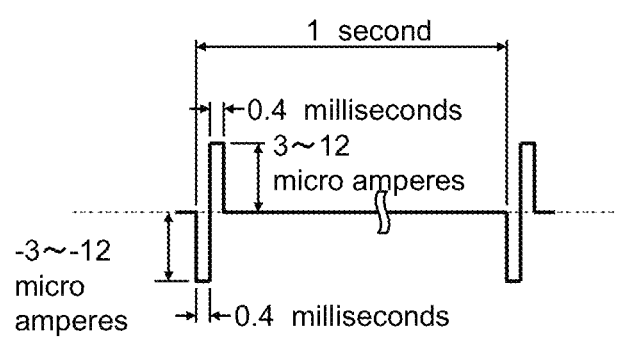
FIG. 3 shows a graph showing an example of desirable pulse electric current.

FIG. 3 is a graph showing an example of a desirable pulse electric current. As shown in FIG. 3, the desirable pulse electric current has a period of 333 milliseconds to 2 seconds (1 second in FIG. 3). One pulse is either positive or negative. In FIG. 3, first, a negative pulse is applied, and then a positive pulse is applied. While the negative pulse is applied, an electric current flows from the cardiac muscle cells to the first electrode 31 (or the second electrode 32). While the positive pulse is applied, an electric current flows from the first electrode 31 (or the second electrode 32) to the cardiac muscle cells.

One pulse has a time length of 0.05 milliseconds to 4 milliseconds (0.4 milliseconds in FIG. 3) and a height (namely, an electric current value) of 1 microampere-20 microamperes (3-12 microamperes, in FIG. 3). It is desirable that the size of the pulse (namely, an area of one pulse in FIG. 3) is not less than 0.1 nano coulomb and not more than 1.0 nano coulomb. More desirably, the rate of the size of the pulse to the area of the first electrode 31 (or the second electrode 32) is not less than 0.04 coulombs/square meter and not more than 0.4 coulombs/square meter. It is desirable that the size of the negative pulse (namely, the area of the negative pulse in FIG. 3) is the same as the size of the positive pulse (namely, the area of the positive pulse in FIG. 3).

As demonstrated in the inventive example 1, the thus-cultivated cardiac muscle cells 180 contain a lot of β MHC.

In other words, the β MHC is produced efficiently in the thus-cultivated cardiac muscle cells 180. In case where the pulse electric current fails to be applied, the β MHC fails to be produced efficiently. See the comparative examples 1, 3, 5, and 7 which will be described later.

EXAMPLES

Hereinafter, the present invention will be described in more detail with reference to the following examples.

(Fabrication of Substrate 100)

Figure 4:
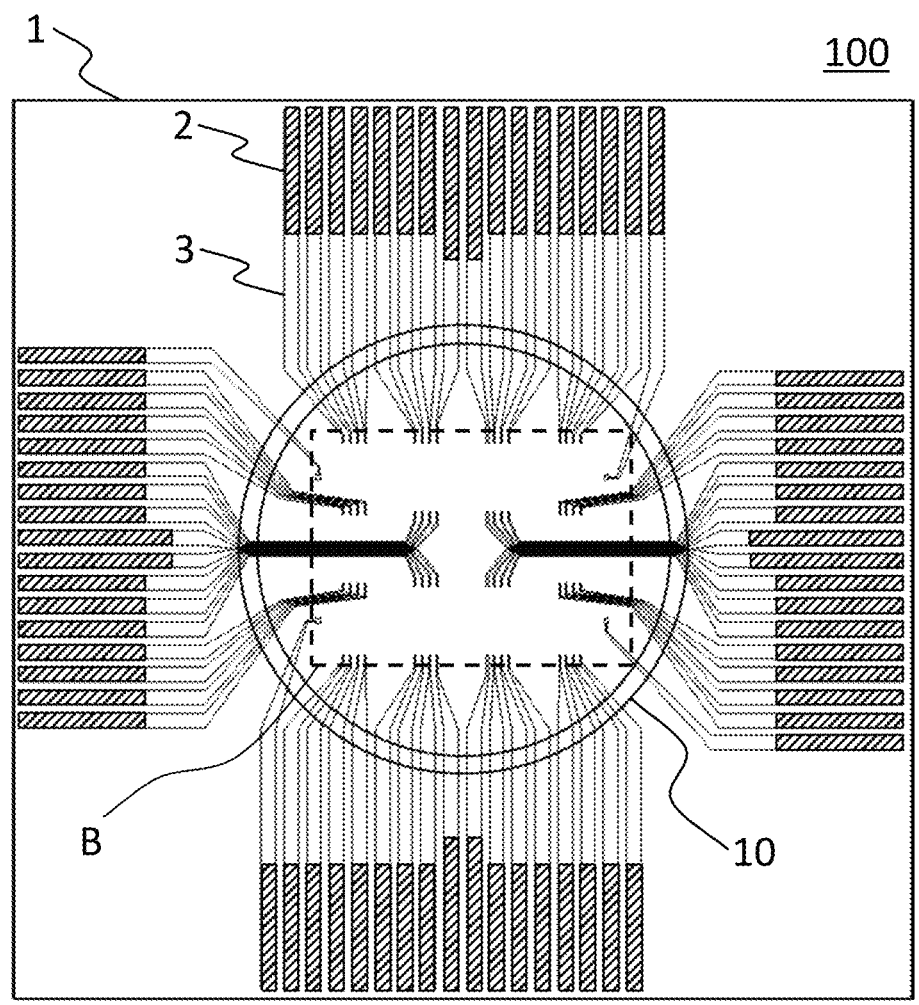
FIG. 4 shows a top view of the substrate in one step included in a method for fabricating the substrate.

The substrate 100 shown in FIG. 1 was fabricated as below. First, the glass base 1 having a shape of a square was prepared. The glass base 1 had a thickness of 0.7 millimeters and an area of approximately 2500 square millimeters (i.e., 50 millimeters×50 millimeters). Then, as shown in FIG. 4, the electric contacts 2 and the electric wirings 3 were formed on the glass base 1. The electric wirings 3 were formed by etching an indium tin oxide film having a thickness of 150 nanometers using a photoresist. The number of the electric contacts 2 and the electric wirings 3 was sixty-eight.

Then, the surface of the glass base 1 was coated with an insulation film 40 consisting of a photosensitive acrylic acid resin. The electric contacts 2 were not coated with the insulation film 40. Each one end of the electric wirings 3 was not coated with the insulation film 40, since the one end of the electric wiring 3 was used as the first electrode 31, the second electrode 32, or the reference electrode 4. Subsequently, the glass base 1 was subjected to plasma surface treatment at an RF power of 18 W for two minutes with a plasma treatment apparatus (available from Harrick Plasma Company, trade name: "PDC-32G").

Figure 5:
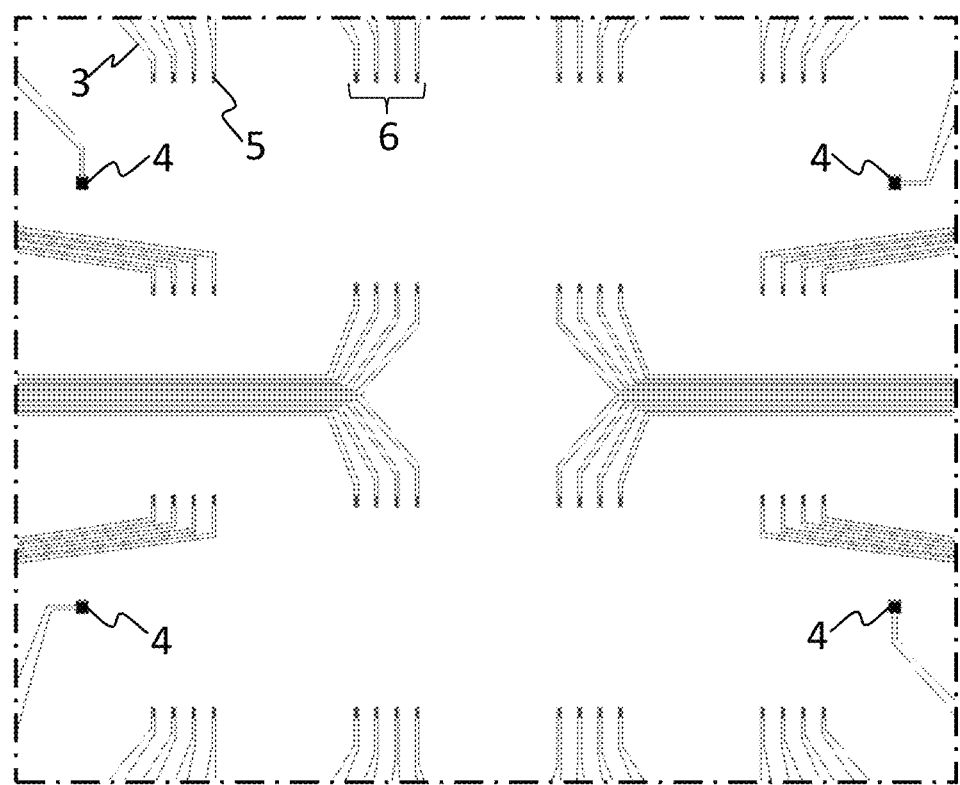
FIG. 5 shows an enlarged view of a region B included in FIG. 4.
Figure 6A:
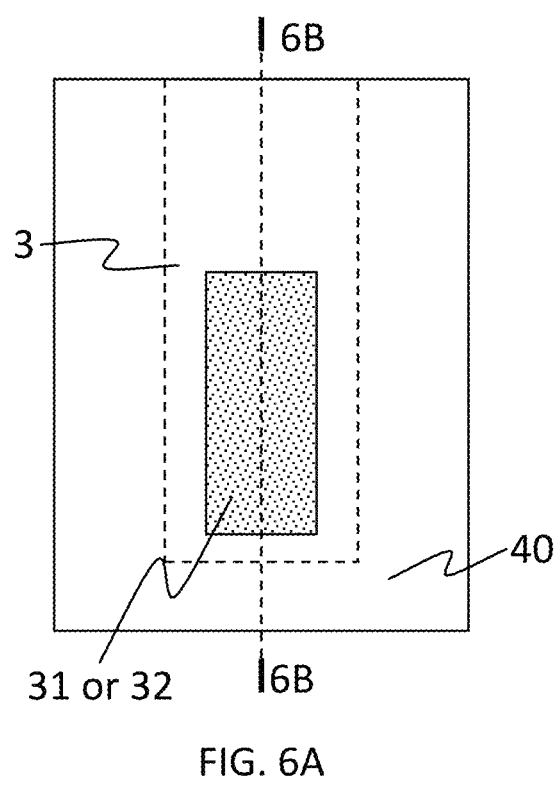
FIG. 6A shows an enlarged top view of an end part of an electric wiring.
Figure 6B:
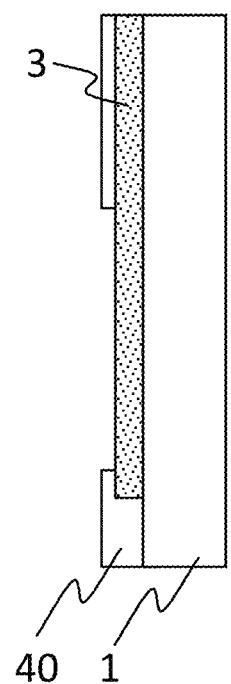
FIG. 6B shows a cross-sectional view taken along the line 6B-6B included in FIG. 6A.

FIG. 5 shows an enlarged view of a region B included in FIG. 4. One electrode set 6 consisted of the ends of the four electric wirings 3, as shown in FIG. 5. The number of the electrode set 6 was 16 sets. The ends of remaining four electric wirings 3 were used for the reference electrode 4. FIG. 6A shows an enlarged top view of the end part of the electric wiring 3. FIG. 6B shows a cross-sectional view taken along the line 6B-6B included in FIG. 6A.

The end of the electric wiring 3 exposed on the surface (i.e., the first electrode 31 and the second electrode 32) had a size of approximately 15 micrometers×approximately 170 micrometers. The reference electrode 4 had an area of approximately 200 square micrometers. The distance between the ends of adjacent two electric wirings 3 was approximately 400 micrometers. The distance of adjacent two electrode sets 6 was approximately 4 millimeters.

Meanwhile, insulative fibers made of polymethyl glutaric imide were formed on the surface of an aluminum tape (available from Hitachi Maxell. Ltd., trade name: SLION-TEC) by an electrospinning method in accordance with the process disclosed in the paragraph 0122 of U.S. patent application Ser. No. 15/519,341. Unlike the process disclosed in the paragraph 0122 of U.S. patent application Ser. No. 15/519,341, an ejection time of polymethyl glutaric imide in the electrospinning method was 30 minutes in the inventive example 1. The insulative fibers had a surface coverage of 30%.

Then, the aluminum tape having the insulative fibers was disposed on the surface of the glass base 1 so that the insulative fibers were sandwiched between the aluminum tape and the electric wiring 3. The aluminum tape having the insulative fibers was impressed onto the surface of the insulation film 40 and the exposed ends of the electric wirings 3. Then, the aluminum tape was removed. FIG. 7A shows an enlarged top view of the end part of the electric wiring 3. FIG. 7B shows a cross-sectional view taken along the line 7B-7B included in FIG. 7A. As shown in FIG. 7A and FIG. 7B, the insulative fibers 50 were transcribed on the surface of the insulation film 40 and the exposed ends of the electric wirings 3. As shown in FIG. 2 and FIG. 7A, not less than 90% of the insulative fibers 50 were disposed in a direction parallel to the imaginary straight line which passes through the first electrode 31 and the second electrode 32 (namely, in a horizontal direction in the figures).

Then, as shown in FIG. 2, a silicone resin sheet 60 (available from Toray Dow Corning company, trade name: SYLGARD 184) was adhered on the insulation film 40 with a silicone adhesive. The silicone resin sheet 60 had a thickness of approximately 1 millimeter. The ends of the electric wirings 3 and their peripheries were not coated with the silicone resin sheet 60. Furthermore, the enclosure 10 was adhered with the silicone adhesive so as to include the silicone resin sheet 60 in the inside thereof. The enclosure 10 was formed of glass. The enclosure 10 had an internal diameter of approximately 22 millimeters, an external diameter of approximately 25 millimeters, and a height of approximately 10 millimeters.

The exposed ends of the electric wirings 3 were plated with platinum black 5. Specifically, the parts were plated at a current density of 20 mA/cm$^2$ for two minutes using a plating solution. During the plating, the electric wirings 3 were used as cathodes. The plating solution had the composition shown in Table 1. The first electrode 31 or the second electrode 32 was formed through such plating on the surface of the end of the electric wiring 3. In other words, the first electrode 31 and the second electrode 32 were formed of platinum black.

TABLE 1

| Composition | Chemical formula | Concentration |
| --- | --- | --- |
| Hexachloroplatinic (IV) acid | $H_2PtCl_6 \cdot 6H_2O$ | 1% |
| Lead acetate | $(CH_3COO)_2Pb \cdot 3H_2O$ | 0.01% |
| Hydrochloric acid | HCl | 0.0025% |

Figure 13A:
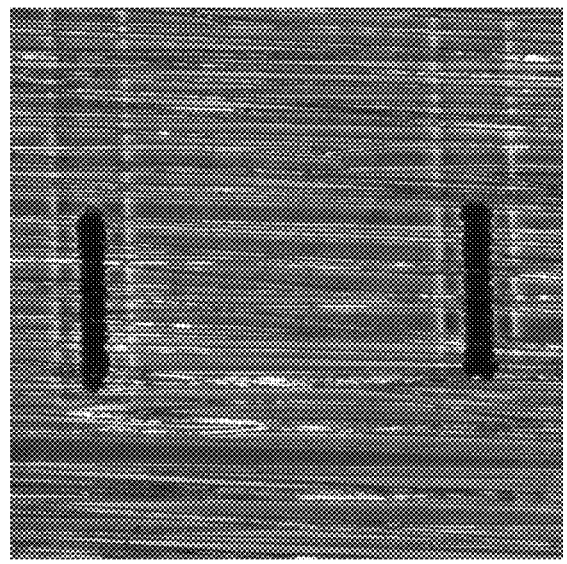
FIG. 13A is a microscope photograph of a first electrode, a second electrode, and an insulative fibers which have been formed on the thus-provided substrate in the inventive example 1.
Figure 13B:
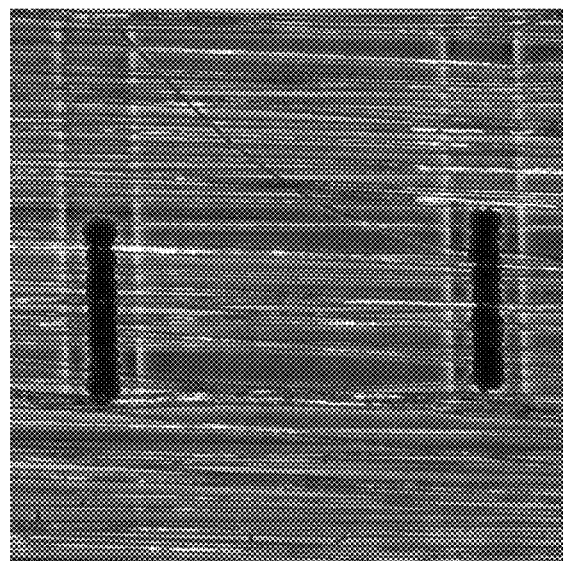
FIG. 13B is another microscope photograph of the first electrode, the second electrode, and the insulative fibers which have been formed on the substrate in the inventive example 1.

In this way, the substrate 100 was provided. FIG. 13A is a microscope photograph of the first electrode 31, the second electrode 32, and the insulative fibers 50 which have been formed on the thus-provided substrate 100. FIG. 13B is also a microscope photograph of the first electrode 31, the second electrode 32, and the insulative fibers 50 which have been formed on the substrate 100 provided similarly. As shown in FIG. 13B, a small amount of non-oriented fibers are included in the insulative fibers 50 due to the problem in the fabrication process by the electrospinning method. The amount of the non-oriented fibers is less than 10%.

(Cultivation of Cardiac Muscle Cells)

Using the substrate 100, cardiac muscle cells differentiated by induced pluripotent stem cells derived from Homo sapiens were cultivated. And then, production ratio of the β MHC was measured. Specifically, cardiac muscle cells differentiated by induced pluripotent stem cells derived from Homo sapiens (available from iPS Academia Japan, Inc., trade name: iCell Cardiomycytes) were used. Pursuant to the protocol described in the manual attached to iCell Cardiomycytes, a liquid culture medium containing cardiac muscle cells differentiated by induced pluripotent stem cells derived from Homo sapiens was prepared.

Then, as shown in FIG. 8A, the liquid culture medium 182 was supplied onto the substrate 100. The density of the cardiac muscle cells 180 on the substrate 100 was 1.5×10$^4$/ square millimeter. In this way, the surface of the first electrode 31, the surface of the second electrode 32, and the region C were coated with the cardiac muscle cells 180. The cardiac muscle cells 180 was cultivated pursuant to the protocol described in the manual attached to iCell Cardiomycytes.

Two days after the supply of the liquid culture medium 182, the pulse electric current shown in FIG. 3 is applied with the reference electrode 4 to the cardiac muscle cells 180 through the first electrode 31 and the second electrode 32 shown in FIG. 2 to stimulate the cardiac muscle cells 180. For the application of the pulse electric current, a pulse electric current generator 200 was electrically connected to the first electrode 31 and the second electrode 32 through the electric contacts 2. The electric potential of the liquid culture medium 182 was maintained at standard electric potential (i.e., GND) through the reference electrode 4.

The pulse electric current was applied to the cardiac muscle cells 180 for 12 days, except in time of a change of a culture medium. In this way, the cardiac muscle cells 180 were cultivated.

(Measurement of Production Ratio of β MHC)

The production ratio of the β MHC contained in the thus-cultivated cardiac muscle cells 180 was measured as below.

The cardiac muscle cells were fixed with 4% paraformaldehyde and were permeabilized in phosphate buffered saline (PBS) plus 0.5% Triton X-100 for 0.5 hours. After blocking in a 5% normal donkey serum, 3% BSA, and 0.1% Tween 20 in PBS for 16 hours at 4 degrees Celsius, the cells were incubated for 16 hours at 4 degrees Celsius with mouse MYH7 monoclonal IgM primary antibodies (available from Santa Cruz Biotechnology, trade name: SC-53089) diluted at 1:100 with a blocking buffer. In this way, the primary antibodies were bound to the cardiac muscle cells. The antigen capable of binding to the primary antibody was β MHC (GenBank: AAA51837.1).

Then, the cardiac muscle cells to which the primary antibodies were bound were washed with PBS. Subsequently, the cardiac muscle cells were incubated for 1 hour at 25 degrees Celsius with fluorescently-labelled anti-mouse IgM secondary antibodies (available from Jackson Immunoresearch labs., trade name: DyLight-594-Donkey anti-mouse IgM) diluted at 1:1,000 with the blocking buffer. In this way, the fluorescently-labelled secondary antibodies were bound to the primary antibodies. In this way, the cardiac muscle cells were fluorescently labelled.

Figure 9A:
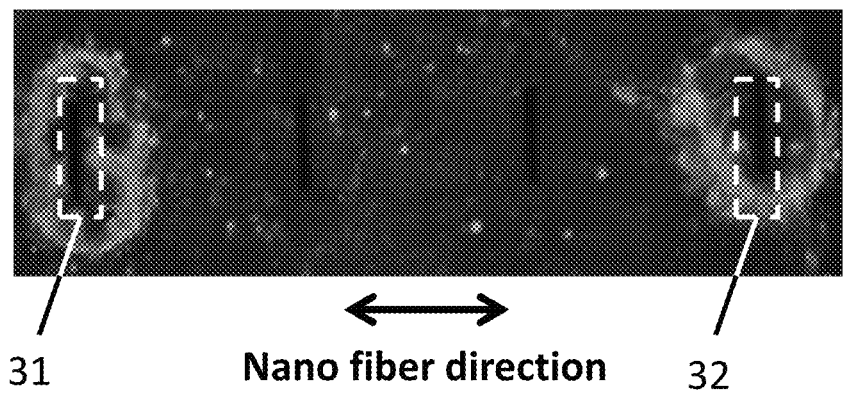
FIG. 9A is a fluorescent microscope photograph of the cardiac muscle cells in the inventive example 1.

The fluorescently-labelled cardiac muscle cells were observed using a fluorescent microscope. FIG. 9A is a fluorescent microscope photograph of the cardiac muscle cells in the inventive example 1. The brightness of the observed fluorescence was converted into 256 gradation digital brightness level. Digital brightness level 0 means that brightness is lowest. Digital brightness level 255 means that brightness is highest.

Hereinafter, the β MHC production ratio is defined as a rate of the sum of the areas of the regions each having a digital brightness level of not less than 65 to the area of the whole of the observation region. In other words, the β MHC production ratio is calculated according to the following mathematical formula.

(β MHC Production Ratio)=(Sum of Areas of the regions each having a digital brightness level of not less than 65)/(Area of the whole of the observation region)

In the inventive example 1, the β MHC production ratio was 57.9%.

For reference, production ratio of myosin regulatory light chain 2 (hereinafter, referred to as "MYL2") contained in the cultivated cardiac muscle cells was measured similarly. In particular, the MYL2 production ratio was calculated similarly to the case of the β MHC production ratio, except for the following two matters.

(I) In place of the mouse MYH7 monoclonal IgM antibodies, rabbit MYL2 polyclonal IgG antibodies (dilution ratio: 1/200, available from Proteintech Company, trade name: 109060-1-AP) was used as the primary antibodies.

(II) In place of the anti-mouse IgM fluorescently-labelled secondary antibodies, anti rabbit IgG fluorescently-labelled antibodies (available from Jackson Immunoresearch labs., trade name: Alexa Fluor 488 Donkey anti-rabbit IgG) was used as the secondary antibodies.

As a result, the MYL2 production ratio was 36.7% in the inventive example 1.

Comparative Example 1

An experiment similar to the inventive example 1 was conducted, except that no pulse electric current was applied.

Comparative Example 2

Figure 9B:
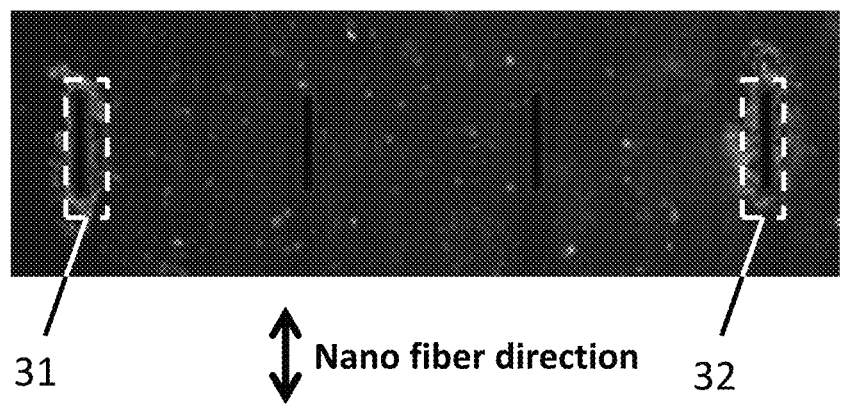
FIG. 9B is a fluorescent microscope photograph of the cardiac muscle cells in the comparative example 2.
Figure 13C:
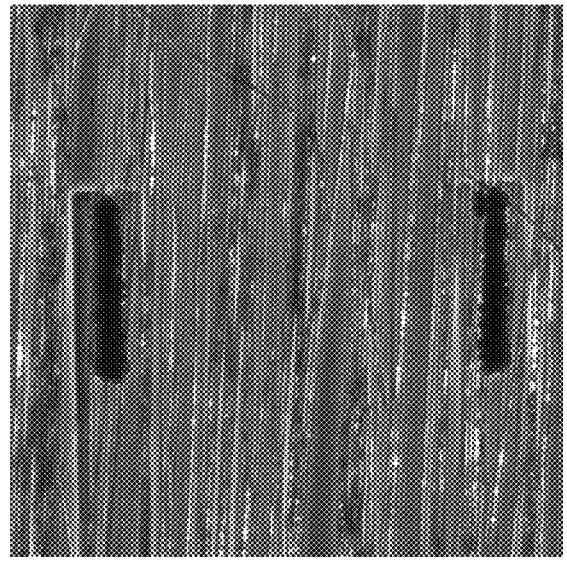
FIG. 13C is a microscope photograph of the first electrode, the second electrode, and the insulative fibers which have been formed on the substrate 100 used in the comparative example 2 and the comparative example 3.

An experiment similar to the inventive example 1 was conducted, except that almost all of the insulative fibers 50 were disposed substantially perpendicularly (namely, in a vertical direction in FIG. 10A) to the imaginary straight line which passes through the first electrode 31 and the second electrode 32, as shown in FIG. 10A and FIG. 10B. FIG. 9B is a fluorescent microscope photograph of the cardiac muscle cells in the comparative example 2. FIG. 13C is a microscope photograph of the first electrode 31, the second electrode 32, and the insulative fibers 50 which have been formed on the thus-obtained substrate 100 used in the comparative example 2 and the comparative example 3 which will be described later. As shown in FIG. 13C, in the comparative examples 2-3, the insulative fibers 50 were disposed in a direction perpendicular to the imaginary straight line which passes through the first electrode 31 and the second electrode 32 (namely, in the vertical direction in the figure).

Comparative Example 3

An experiment similar to the inventive example 1 was conducted, except that almost all of the insulative fibers 50 were disposed substantially perpendicularly (namely, in a vertical direction in FIG. 10A) to the imaginary straight line which passes through the first electrode 31 and the second electrode 32, as shown in FIG. 10A and FIG. 10B, and except that no pulse electric current was applied.

Comparative Example 4

Figure 9C:
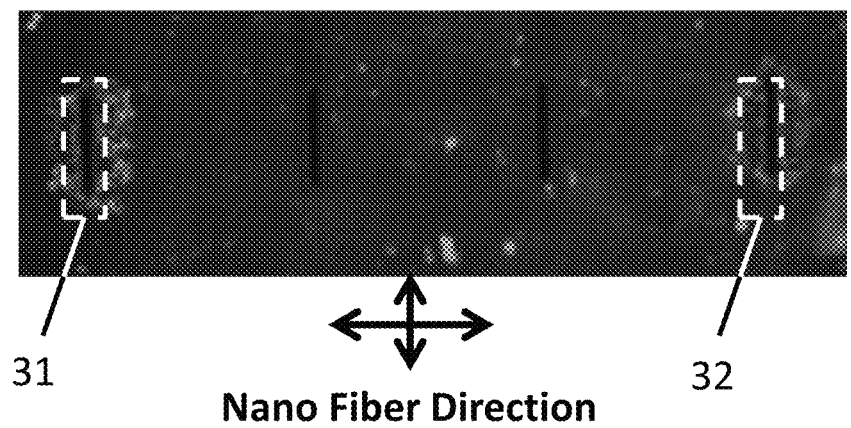
FIG. 9C is a fluorescent microscope photograph of the cardiac muscle cells in the comparative example 4.
Figure 11A:
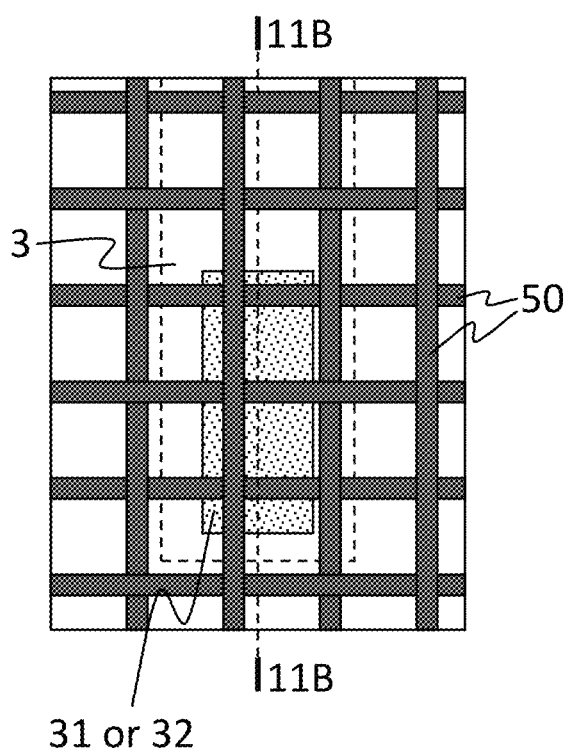
FIG. 11A shows an enlarged top view of the end part of the electric wiring in the comparative examples 4 and 5.
Figure 11B:
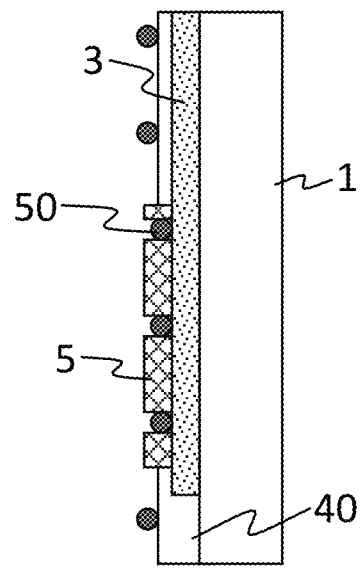
FIG. 11B shows a cross-sectional view taken along the line 11B-11B included in FIG. 11A.
Figure 13D:
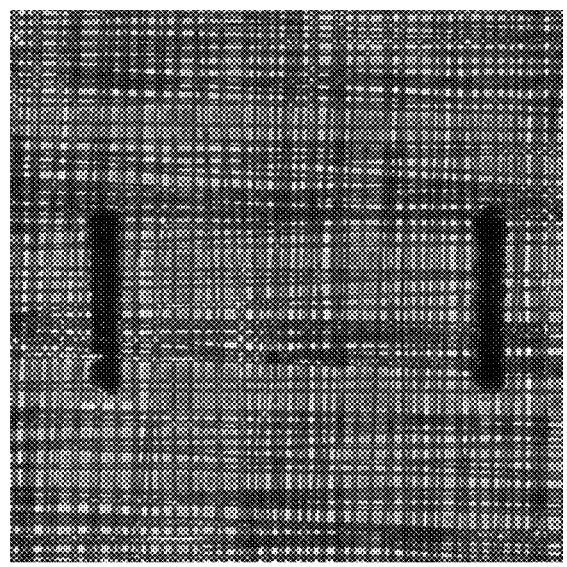
FIG. 13D is a microscope photograph of the first electrode, the second electrode, and the insulative fibers which have been formed on the provided substrate used in the comparative example 4 and the comparative example 5.

An experiment similar to the inventive example 1 was conducted, except that roughly half of the insulative fibers 50 were disposed parallel (namely, in the horizontal direction in FIG. 11A) to the imaginary straight line which passes through the first electrode 31 and the second electrode 32 and the other roughly half of the insulative fibers 50 were disposed perpendicularly (namely, in a vertical direction in FIG. 11A) to the imaginary straight line, as shown in FIG. 11A and FIG. 11B. FIG. 9C is a fluorescent microscope photograph of the cardiac muscle cells in the comparative example 4. FIG. 13D is a microscope photograph of the first electrode 31, the second electrode 32, and the insulative fibers 50 which have been formed on the thus-obtained substrate 100 used in the comparative example 4 and the comparative example 5 which will be described later. As shown in FIG. 13D, in the comparative examples 4-5, roughly half of the insulative fibers 50 (ejection time: 15 minutes) were disposed in a direction parallel to the imaginary straight line which passes through the first electrode 31 and the second electrode 32 (namely, in the horizontal direction in the figure), whereas the other roughly half of the insulative fibers 50 (ejection time: 15 minutes) were disposed in a direction perpendicular to the imaginary straight line (namely, in the vertical direction in the figure).

Comparative Example 5

An experiment similar to the inventive example 1 was conducted, except that some of the insulative fibers 50 were disposed parallel (namely, in the horizontal direction in FIG. 11A) to the imaginary straight line which passes through the first electrode 31 and the second electrode 32 and the other insulative fibers 50 were disposed perpendicularly (namely, in a vertical direction in FIG. 11A) to the imaginary straight line, as shown in FIG. 11A and FIG. 11B, and except that no pulse electric current was applied.

Comparative Example 6

Figure 9D:
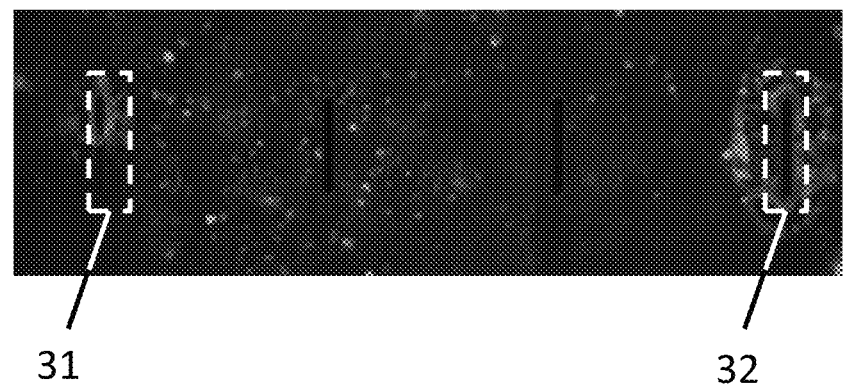
FIG. 9D is a fluorescent microscope photograph of the cardiac muscle cells in the comparative example 6.
Figure 12A:
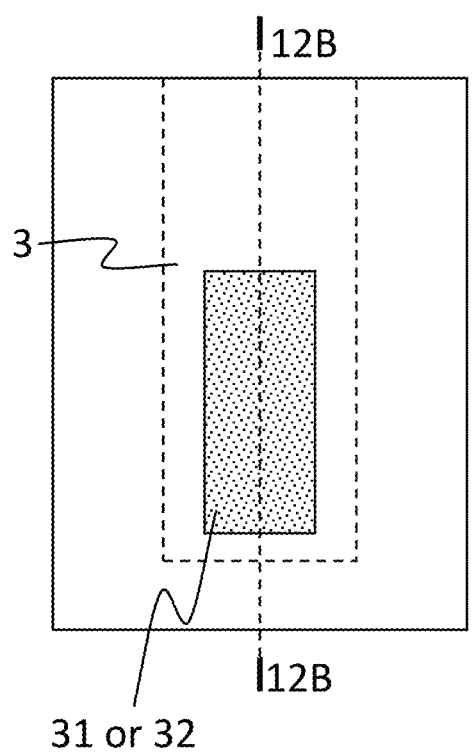
FIG. 12A shows an enlarged top view of the end part of the electric wiring in the comparative examples 6 and 7.
Figure 12B:
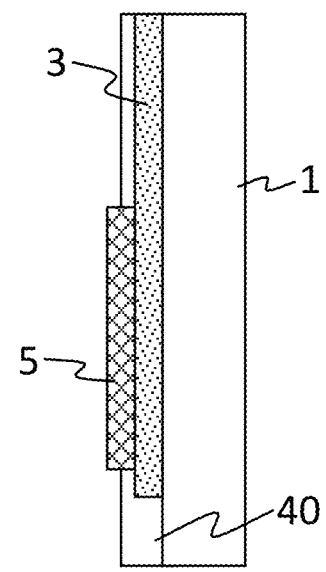
FIG. 12B shows a cross-sectional view taken along the line 12B-12B included in FIG. 12A.

An experiment similar to the inventive example 1 was conducted, except that no insulative fibers 50 were disposed, as shown in FIG. 12A and FIG. 12B. FIG. 9D is a fluorescent microscope photograph of the cardiac muscle cells in the comparative example 6.

Comparative Example 7

An experiment similar to the inventive example 1 was conducted, except that no insulative fibers 50 were disposed, as shown in FIG. 12A and FIG. 12B, and except that no pulse electric current was applied.

The following Table 2 shows the 13 WIC production rate measured in the inventive example 1 and the comparative examples 1-7.

TABLE 2

| | Relation Between Direction of Insulative fibers and Direction of Electric Field | Pulse electric current | β MHC production rate (%) |
|---|---|---|---|
| I.E. 1 | FIG. 13A or FIG. 13B | Applied | 57.9 |
| C.E. 1 | FIG. 13A or FIG. 13B | No | 14.5 |
| C.E. 2 | FIG. 13C | Applied | 31.9 |
| C.E. 3 | FIG. 13C | No | 10.3 |
| C.E. 4 | FIG. 13D | Applied | 36.5 |
| C.E. 5 | FIG. 13D | No | 15.8 |
| C.E. 6 | No insulative fibers | Applied | 15.4 |
| C.E. 7 | No insulative fibers | No | 9.8 |

"I.E." means "Inventive Example".
"C.E." means "Comparative Example".
"Electric Field" means the electric field generated between the first electrode 31 and the second electrode 32 by the electric current pulse.

The following Table 3 shows the MYL2 production rate measured in the inventive example 1 and the comparative examples 1-7.

TABLE 3

| | Relation Between Direction of Insulative fibers and Direction of Electric Field | Pulse electric current | MYL2 production rate (%) |
|---|---|---|---|
| I.E. 1 | FIG. 13A or FIG. 13B | Applied | 36.7 |
| C.E. 1 | FIG. 13A or FIG. 13B | No | 25.1 |
| C.E. 2 | FIG. 13C | Applied | 30.0 |
| C.E. 3 | FIG. 13C | No | 19.0 |
| C.E. 4 | FIG. 13D | Applied | 32.5 |
| C.E. 5 | FIG. 13D | No | 24.0 |
| C.E. 6 | No insulative fibers | Applied | 16.2 |
| C.E. 7 | No insulative fibers | No | 10.1 |

As is clear from Table 2, when both of the following requirements (I) and (II) are satisfied, the β MHC production rate is a significantly high value of 57.9%. See the inventive example 1.

Requirement (I): The insulative fibers 50 have orientation such that an angle formed between each of not less than 90% of the insulative fibers 50 and an imaginary straight line which passes through both the first electrode 31 and the second electrode 32 is not more than ±20 degrees in the top view.

Requirement (II): The cardiac muscle cells 180 are cultivated, while the pulse electric current is applied thereto.

On the other hand, in case where at least one of the requirements (I) and (II) fails to be satisfied, the β MHC production rate is a low value of less than 36.5%. See the comparative examples 1-7.

As is clear from Table 3, regardless to the direction of the insulative fibers, the MYL2 production rate is a constant value of approximately 32%-37%. On the other hand, as is clear from Table 1, the β MHC production rate is significantly increased, when both of the requirements (I) and (II) are satisfied. In other words, the use of the insulative fibers increases the production amount of polypeptide (including protein) in the cardiac muscle cells. Among the polypeptide produced in the cardiac muscle cells, when both of the requirements (I) and (II) are satisfied, the β MHC is produced at the significantly high production rate, unlike other polypeptide such as MYL2.

INDUSTRIAL APPLICABILITY

The present invention provides a method for efficiently producing β myosin heavy chain in cardiac muscle cells differentiated from induced pluripotent stem cells derived from Homo sapiens.

REFERENTIAL SIGNS LIST

100 Substrate
1 Glass plate
2 Electric contact
3 Electric wiring
4 Reference electrode
5 Platinum black
6 Electrode set
10 Enclosure
31 First electrode
32 Second electrode
40 Insulation film
50 Insulative fiber
60 Insulative sheet
A Region
B Region C Region
180 Cardiac muscle cells
182 Liquid culture medium
200 Pulse electric current generator

---

SEQUENCE LISTING

---

```
<110> Panasonic Corporation
<120> METHOD FOR EFFICIENTLY PRODUCING BETA MYOSIN HEAVY CHAIN IN
CARDIAC MUSCLE CELLS DIFFERENTIATED FROM INDUCED PLURIPOTENT STEM
CELLS DERIVED FROM HOMO SAPIENS
<130> P1006798US01
<160> 2
<170> PatentIn version 3.5
<210> 1
<211> 1935
<212> PRT
<213> Homo sapiens
<400> 1
Met Gly Asp Ser Glu Met Ala Val Phe Gly Ala Ala Pro Tyr Leu
1               5                   10                  15
Arg Lys Ser Glu Lys Glu Arg Leu Glu Ala Gln Thr Arg Pro Phe Asp
            20                  25                  30
Leu Lys Lys Asp Val Phe Val Pro Asp Asp Lys Gln Glu Phe Val Lys
            35                  40                  45
Ala Lys Ile Val Ser Arg Glu Gly Gly Lys Val Thr Ala Glu Thr Glu
            50                  55                  60
Tyr Gly Lys Thr Val Thr Val Lys Glu Asp Gln Val Met Gln Gln Asn
65                  70                  75                  80
Pro Pro Lys Phe Asp Lys Ile Glu Asp Met Ala Met Leu Thr Phe Leu
                85                  90                  95
His Glu Pro Ala Val Leu Tyr Asn Leu Lys Asp Arg Tyr Gly Ser Trp
            100                 105                 110
Met Ile Tyr Thr Tyr Ser Gly Leu Phe Cys Val Thr Val Asn Pro Tyr
            115                 120                 125
Lys Trp Leu Pro Val Tyr Thr Pro Glu Val Val Ala Ala Tyr Arg Gly
            130                 135                 140
Lys Lys Arg Ser Glu Ala Pro Pro His Ile Phe Ser Ile Ser Asp Asn
145                 150                 155                 160
Ala Tyr Gln Tyr Met Leu Thr Asp Arg Glu Asn Gln Ser Ile Leu Ile
                165                 170                 175
Thr Gly Glu Ser Gly Ala Gly Lys Thr Val Asn Thr Lys Arg Val Ile
            180                 185                 190
Gln Tyr Phe Ala Val Ile Ala Ala Ile Gly Asp Arg Ser Lys Lys Asp
            195                 200                 205
Gln Ser Pro Gly Lys Gly Thr Leu Glu Asp Gln Ile Ile Gln Ala Asn
            210                 215                 220
Pro Ala Leu Glu Ala Phe Gly Asn Ala Lys Thr Val Arg Asn Asp Asn
225                 230                 235                 240
Ser Ser Arg Phe Gly Lys Phe Ile Arg Ile His Phe Gly Ala Thr Gly
                245                 250                 255
Lys Leu Ala Ser Ala Asp Ile Glu Thr Tyr Leu Leu Glu Lys Ser Arg
            260                 265                 270
Val Ile Phe Gln Leu Lys Ala Glu Arg Asp Tyr His Ile Phe Tyr Gln
            275                 280                 285
Ile Leu Ser Asn Lys Lys Pro Glu Leu Leu Asp Met Leu Leu Ile Thr
            290                 295                 300
Asn Asn Pro Tyr Asp Tyr Ala Phe Ile Ser Gln Gly Glu Thr Thr Val
305                 310                 315                 320
Ala Ser Ile Asp Asp Ala Glu Glu Leu Met Ala Thr Asp Asn Ala Phe
                325                 330                 335
Asp Val Leu Gly Phe Thr Ser Glu Glu Lys Asn Ser Met Tyr Lys Leu
            340                 345                 350
Thr Gly Ala Ile Met His Phe Gly Asn Met Lys Phe Lys Leu Lys Gln
            355                 360                 365
Arg Glu Glu Gln Ala Glu Pro Asp Gly Thr Glu Glu Ala Asp Lys Ser
            370                 375                 380
Ala Tyr Leu Met Gly Leu Asn Ser Ala Asp Leu Leu Lys Gly Leu Cys
385                 390                 395                 400
His Pro Arg Val Lys Val Gly Asn Glu Tyr Val Thr Lys Gly Gln Asn
                405                 410                 415
Val Gln Gln Val Ile Tyr Ala Thr Gly Ala Leu Ala Lys Ala Val Tyr
            420                 425                 430
Glu Arg Met Phe Asn Trp Met Val Thr Arg Ile Asn Ala Thr Leu Glu
            435                 440                 445
Thr Lys Gln Pro Arg Gln Tyr Phe Ile Gly Val Leu Asp Ile Ala Gly
            450                 455                 460
Phe Glu Ile Phe Asp Phe Asn Ser Phe Glu Gln Leu Cys Ile Asn Phe
465                 470                 475                 480
Thr Asn Glu Lys Leu Gln Gln Phe Phe Asn His His Met Phe Val Leu
```

SEQUENCE LISTING

```
                      485                 490                 495
Glu Gln Glu Glu Tyr Lys Lys Glu Gly He Glu Trp Thr Phe Ile Asp
                  500                 505                 510
Phe Gly Met Asp Leu Gln Ala Cys Ile Asp Leu Ile Glu Lys Pro Met
              515                 520                 525
Gly Ile Met Ser Ile Leu Glu Glu Cys Met Phe Pro Lys Ala Thr
          530                 535                 540
Asp Met Thr Phe Lys Ala Lys Leu Phe Asp Asn His Leu Gly Lys Ser
545                 550                 555                 560
Ala Asn Phe Gln Lys Pro Arg Asn Ile Lys Gly Lys Pro Glu Ala His
                  565                 570                 575
Phe Ser Leu Ile His Tyr Ala Gly Ile Val Asp Tyr Asn Ile Ile Gly
              580                 585                 590
Trp Leu Gln Lys Asn Lys Asp Pro Leu Asn Glu Thr Val Val Gly Leu
          595                 600                 605
Tyr Gln Lys Ser Ser Leu Lys Leu Leu Ser Thr Leu Phe Ala Asn Tyr
          610                 615                 620
Ala Gly Ala Asp Ala Pro Ile Glu Lys Gly Lys Gly Lys Ala Lys Lys
625                 630                 635                 640
Gly Ser Ser Phe Gln Thr Val Ser Ala Leu His Arg Glu Asn Leu Asn
                  645                 650                 655
Lys Leu Met Thr Asn Leu Arg Ser Thr His Pro His Phe Val Arg Cys
              660                 665                 670
Ile Ile Pro Asn Glu Thr Lys Ser Pro Gly Val Met Asp Asn Pro Leu
          675                 680                 685
Val Met His Gln Leu Arg Cys Asn Gly Val Leu Glu Gly Ile Arg Ile
          690                 695                 700
Cys Arg Lys Gly Phe Pro Asn Arg Ile Leu Tyr Gly Asp Phe Arg Gln
705                 710                 715                 720
Arg Tyr Arg Ile Leu Asn Pro Ala Ala Ile Pro Glu Gly Gln Phe Ile
                  725                 730                 735
Asp Ser Arg Lys Gly Ala Glu Lys Leu Leu Ser Ser Leu Asp Ile Asp
              740                 745                 750
His Asn Gln Tyr Lys Phe Gly His Thr Lys Val Phe Phe Lys Ala Gly
          755                 760                 765
Leu Leu Gly Leu Leu Glu Glu Met Arg Asp Glu Arg Leu Ser Arg Ile
          770                 775                 780
Ile Thr Arg Ile Gln Ala Gln Ser Arg Gly Val Leu Ala Arg Met Glu
785                 790                 795                 800
Tyr Lys Lys Leu Leu Glu Arg Arg Asp Ser Leu Leu Val Ile Gln Trp
                  805                 810                 815
Asn Ile Arg Ala Phe Met Gly Val Lys Asn Trp Pro Trp Met Lys Leu
              820                 825                 830
Tyr Phe Lys Ile Lys Pro Leu Leu Lys Ser Ala Glu Arg Glu Lys Glu
          835                 840                 845
Met Ala Ser Met Lys Glu Glu Phe Thr Arg Leu Lys Glu Ala Leu Glu
          850                 855                 860
Lys Ser Glu Ala Arg Arg Lys Glu Leu Glu Glu Lys Met Val Ser Leu
865                 870                 875                 880
Leu Gln Glu Lys Asn Asp Leu Gln Leu Gln Val Gln Ala Glu Gln Asp
                  885                 890                 895
Asn Leu Ala Asp Ala Glu Glu Arg Cys Asp Gln Leu Ile Lys Asn Lys
              900                 905                 910
Ile Gln Leu Glu Ala Lys Val Lys Glu Met Asn Glu Arg Leu Glu Asp
          915                 920                 925
Glu Glu Glu Met Asn Ala Glu Leu Thr Ala Lys Lys Arg Lys Leu Glu
          930                 935                 940
Asp Glu Cys Ser Glu Leu Lys Arg Asp Ile Asp Asp Leu Glu Leu Thr
945                 950                 955                 960
Leu Ala Lys Val Glu Lys Glu Lys His Ala Thr Glu Asn Lys Val Lys
                  965                 970                 975
Asn Leu Thr Glu Glu Met Ala Gly Leu Asp Glu Ile Ile Ala Lys Leu
              980                 985                 990
Thr Lys Glu Lys Lys Ala Leu Gln Glu Ala His Gln Gln Ala Leu Asp
          995                 1000                1005
Asp Leu Gln Ala Glu Glu Asp Lys Val Asn Thr Leu Thr Lys Ala
          1010                1015                1020
Lys Val Lys Leu Glu Gln Gln Val Asp Asp Leu Glu Gly Ser Leu
          1025                1030                1035
Glu Gln Glu Lys Lys Val Arg Met Asp Leu Glu Arg Ala Lys Arg
          1040                1045                1050
Lys Leu Glu Gly Asp Leu Lys Leu Thr Gln Glu Ser He Met Asp
          1055                1060                1065
Leu Glu Asn Asp Lys Gln Gln Leu Asp Glu Arg Leu Lys Lys Lys
          1070                1075                1080
Asp Phe Glu Leu Asn Ala Leu Asn Ala Arg Ile Glu Asp Glu Gln
          1085                1090                1095
```

SEQUENCE LISTING

```
Ala Leu Gly Ser Gln Leu Gln Lys Lys Leu Lys Glu Leu Gln Ala
            1100                1105                1110
Arg Ile Glu Glu Leu Glu Glu Leu Glu Ser Glu Arg Thr Ala
    1115                1120                1125
Arg Ala Lys Val Glu Lys Leu Arg Ser Asp Leu Ser Arg Glu Leu
            1130                1135                1140
Glu Glu Ile Ser Glu Arg Leu Glu Glu Ala Gly Gly Ala Thr Ser
            1145                1150                1155
Val Gln Ile Glu Met Asn Lys Lys Arg Glu Ala Glu Phe Gln Lys
            1160                1165                1170
Met Arg Arg Asp Leu Glu Glu Ala Thr Leu Gln His Glu Ala Thr
    1175                1180                1185
Ala Ala Ala Leu Arg Lys Lys His Ala Asp Ser Val Ala Glu Leu
            1190                1195                1200
Gly Glu Gln Ile Asp Asn Leu Gln Arg Val Lys Gln Lys Leu Glu
            1205                1210                1215
Lys Glu Lys Ser Glu Phe Lys Leu Glu Leu Asp Asp Val Thr Ser
            1220                1225                1230
Asn Met Glu Gln Ile Ile Lys Ala Lys Ala Asn Leu Glu Lys Met
            1235                1240                1245
Cys Arg Thr Leu Glu Asp Gln Met Asn Glu His Arg Ser Lys Ala
            1250                1255                1260
Glu Glu Thr Gln Arg Ser Val Asn Asp Leu Thr Ser Gln Arg Ala
            1265                1270                1275
Lys Leu Gln Thr Glu Asn Gly Glu Leu Ser Arg Gln Leu Asp Glu
            1280                1285                1290
Lys Glu Ala Leu Ile Ser Gln Leu Thr Arg Gly Lys Leu Thr Tyr
            1295                1300                1305
Thr Gln Gln Leu Glu Asp Leu Lys Arg Gln Leu Glu Glu Glu Val
            1310                1315                1320
Lys Ala Lys Asn Ala Leu Ala His Ala Leu Gln Ser Ala Arg His
            1325                1330                1335
Asp Cys Asp Leu Leu Arg Glu Gln Tyr Glu Glu Thr Glu Ala
            1340                1345                1350
Lys Ala Glu Leu Gln Arg Val Leu Ser Lys Ala Asn Ser Glu Val
            1355                1360                1365
Ala Gln Trp Arg Thr Lys Tyr Glu Thr Asp Ala Ile Gln Arg Thr
            1370                1375                1380
Glu Glu Leu Glu Glu Ala Lys Lys Lys Leu Ala Gln Arg Leu Gln
            1385                1390                1395
Glu Ala Glu Glu Ala Val Glu Ala Val Asn Ala Lys Cys Ser Ser
            1400                1405                1410
Leu Glu Lys Thr Lys His Arg Leu Gln Asn Glu Ile Glu Asp Leu
            1415                1420                1425
Met Val Asp Val Glu Arg Ser Asn Ala Ala Ala Ala Ala Leu Asp
            1430                1435                1440
Lys Lys Gln Arg Asn Phe Asp Lys Ile Leu Ala Glu Trp Lys Gln
            1445                1450                1455
Lys Tyr Glu Glu Ser Gln Ser Glu Leu Glu Ser Ser Gln Lys Glu
            1460                1465                1470
Ala Arg Ser Leu Ser Thr Glu Leu Phe Lys Leu Lys Asn Ala Tyr
            1475                1480                1485
Glu Glu Ser Leu Glu His Leu Glu Thr Phe Lys Arg Glu Asn Lys
            1490                1495                1500
Asn Leu Gln Glu Glu Ile Ser Asp Leu Thr Glu Gln Leu Gly Ser
            1505                1510                1515
Ser Gly Lys Thr Ile His Glu Leu Glu Lys Val Arg Lys Gln Leu
            1520                1525                1530
Glu Ala Glu Lys Met Glu Leu Gln Ser Ala Leu Glu Glu Ala Glu
            1535                1540                1545
Ala Ser Leu Glu His Glu Glu Gly Lys Ile Leu Arg Ala Gln Leu
            1550                1555                1560
Glu Phe Asn Gln Ile Lys Ala Glu Ile Glu Arg Lys Leu Ala Glu
            1565                1570                1575
Lys Asp Glu Glu Met Glu Gln Ala Lys Arg Asn His Leu Arg Val
            1580                1585                1590
Val Asp Ser Leu Gln Thr Ser Leu Asp Ala Glu Thr Arg Ser Arg
            1595                1600                1605
Asn Glu Ala Leu Arg Val Lys Lys Lys Met Glu Gly Asp Leu Asn
            1610                1615                1620
Glu Met Glu Ile Gln Leu Ser His Ala Asn Arg Met Ala Ala Glu
            1625                1630                1635
Ala Gln Lys Gln Val Lys Ser Leu Gln Ser Leu Leu Lys Asp Thr
            1640                1645                1650
Gln Ile Gln Leu Asp Asp Ala Val Arg Ala Asn Asp Asp Leu Lys
            1655                1660                1665
Glu Asn Ile Ala Ile Val Glu Arg Arg Asn Asn Leu Leu Gln Ala
```

SEQUENCE LISTING

```
              1670                1675                1680
Glu Leu Glu Glu Leu Arg Ala Val Val Glu Gln Thr Glu Arg Ser
          1685                1690                1695
Arg Lys Leu Ala Glu Gln Glu Leu Ile Glu Thr Ser Glu Arg Val
      1700                1705                1710
Gln Leu Leu His Ser Gln Asn Thr Ser Leu Ile Asn Gln Lys Lys
  1715                1720                1725
Lys Met Asp Ala Asp Leu Ser Gln Leu Gln Thr Glu Val Glu Glu
      1730                1735                1740
Ala Val Gln Glu Cys Arg Asn Ala Glu Lys Ala Lys Lys Ala
  1745                1750                1755
Ile Thr Asp Ala Ala Met Met Ala Glu Leu Lys Lys Glu Gln
      1760                1765                1770
Asp Thr Ser Ala His Leu Glu Arg Met Lys Lys Asn Met Glu Gln
  1775                1780                1785
Thr Ile Lys Asp Leu Gln His Arg Leu Asp Glu Ala Glu Gln Ile
      1790                1795                1800
Ala Leu Lys Gly Gly Lys Lys Gln Leu Gln Lys Leu Glu Ala Arg
  1805                1810                1815
Val Arg Glu Leu Glu Asn Glu Leu Glu Ala Glu Gln Lys Arg Asn
      1820                1825                1830
Ala Glu Ser Val Lys Gly Met Arg Lys Ser Glu Arg Arg Ile Lys
  1835                1840                1845
Glu Leu Thr Tyr Gln Thr Glu Glu Asp Arg Lys Asn Leu Leu Arg
      1850                1855                1860
Leu Gln Asp Leu Val Asp Lys Leu Gln Leu Lys Val Lys Ala Tyr
  1865                1870                1875
Lys Arg Gln Ala Glu Glu Ala Glu Glu Gln Ala Asn Thr Asn Leu
      1880                1885                1890
Ser Lys Phe Arg Lys Val Gln His Glu Leu Asp Glu Ala Glu Glu
  1895                1900                1905
Arg Ala Asp Ile Ala Glu Ser Gln Val Asn Lys Leu Arg Ala Lys
      1910                1915                1920
Ser Arg Asp Ile Gly Thr Lys Gly Leu Asn Glu Glu
  1925                1930                1935

<210> 2
<211> 166
<212> PRT
<213> Homo sapiens
<400> 2
Met Ala Pro Lys Lys Ala Lys Lys Arg Ala Gly Gly Ala Asn Ser Asn
1               5                   10                  15
Val Phe Ser Met Phe Glu Gln Thr Gln Ile Gln Glu Phe Lys Glu Ala
            20                  25                  30
Phe Thr Ile Met Asp Gln Asn Arg Asp Gly Phe Ile Asp Lys Asn Asp
        35                  40                  45
Leu Arg Asp Thr Phe Ala Ala Leu Gly Arg Val Asn Val Lys Asn Glu
    50                  55                  60
Glu Ile Asp Glu Met Ile Lys Glu Ala Pro Gly Pro Ile Asn Phe Thr
65                  70                  75                  80
Val Phe Leu Thr Met Phe Gly Glu Lys Leu Lys Gly Ala Asp Pro Glu
                85                  90                  95
Glu Thr Ile Leu Asn Ala Phe Lys Val Phe Asp Pro Glu Gly Lys Gly
            100                 105                 110
Val Leu Lys Ala Asp Tyr Val Arg Glu Met Leu Thr Thr Gln Ala Glu
        115                 120                 125
Arg Phe Ser Lys Gly Glu Val Asp Gln Met Phe Ala Ala Phe Pro Pro
    130                 135                 140
Asp Val Thr Gly Asn Leu Asp Tyr Lys Asn Leu Val His Ile Ile Thr
145                 150                 155                 160
His Gly Glu Glu Lys Asp
                165
```

SEQUENCE LISTING

<160> NUMBER OF SEQ ID NOS: 2

<210> SEQ ID NO 1
<211> LENGTH: 1935
<212> TYPE: PRT
<213> ORGANISM: Homo sapiens

```
<400> SEQUENCE: 1

Met Gly Asp Ser Glu Met Ala Val Phe Gly Ala Ala Pro Tyr Leu
1               5                   10                  15

Arg Lys Ser Glu Lys Glu Arg Leu Glu Ala Gln Thr Arg Pro Phe Asp
            20                  25                  30

Leu Lys Lys Asp Val Phe Val Pro Asp Asp Lys Gln Glu Phe Val Lys
            35                  40                  45

Ala Lys Ile Val Ser Arg Glu Gly Gly Lys Val Thr Ala Glu Thr Glu
        50                  55                  60

Tyr Gly Lys Thr Val Thr Val Lys Glu Asp Gln Val Met Gln Gln Asn
65                  70                  75                  80

Pro Pro Lys Phe Asp Lys Ile Glu Asp Met Ala Met Leu Thr Phe Leu
                85                  90                  95

His Glu Pro Ala Val Leu Tyr Asn Leu Lys Asp Arg Tyr Gly Ser Trp
            100                 105                 110

Met Ile Tyr Thr Tyr Ser Gly Leu Phe Cys Val Thr Val Asn Pro Tyr
            115                 120                 125

Lys Trp Leu Pro Val Tyr Thr Pro Glu Val Val Ala Ala Tyr Arg Gly
130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
            180                 185                 190

Gln Tyr Phe Ala Val Ile Ala Ala Ile Gly Asp Arg Ser Lys Lys Asp
        195                 200                 205

Gln Ser Pro Gly Lys Gly Thr Leu Glu Asp Gln Ile Ile Gln Ala Asn
210                 215                 220

Pro Ala Leu Glu Ala Phe Gly Asn Ala Lys Thr Val Arg Asn Asp Asn
225                 230                 235                 240

Ser Ser Arg Phe Gly Lys Phe Ile Arg Ile His Phe Gly Ala Thr Gly
                245                 250                 255

Lys Leu Ala Ser Ala Asp Ile Glu Thr Tyr Leu Leu Glu Lys Ser Arg
            260                 265                 270

Val Ile Phe Gln Leu Lys Ala Glu Arg Asp Tyr His Ile Phe Tyr Gln
        275                 280                 285

Ile Leu Ser Asn Lys Lys Pro Glu Leu Leu Asp Met Leu Leu Ile Thr
290                 295                 300

Asn Asn Pro Tyr Asp Tyr Ala Phe Ile Ser Gln Gly Glu Thr Thr Val
305                 310                 315                 320

Ala Ser Ile Asp Asp Ala Glu Glu Leu Met Ala Thr Asp Asn Ala Phe
                325                 330                 335

Asp Val Leu Gly Phe Thr Ser Glu Glu Lys Asn Ser Met Tyr Lys Leu
            340                 345                 350

Thr Gly Ala Ile Met His Phe Gly Asn Met Lys Phe Lys Leu Lys Gln
        355                 360                 365

Arg Glu Glu Gln Ala Glu Pro Asp Gly Thr Glu Ala Asp Lys Ser
370                 375                 380

Ala Tyr Leu Met Gly Leu Asn Ser Ala Asp Leu Leu Lys Gly Leu Cys
385                 390                 395                 400

His Pro Arg Val Lys Val Gly Asn Glu Tyr Val Thr Lys Gly Gln Asn
                405                 410                 415
```

-continued

Val Gln Gln Val Ile Tyr Ala Thr Gly Ala Leu Ala Lys Ala Val Tyr
                420                 425                 430

Glu Arg Met Phe Asn Trp Met Val Thr Arg Ile Asn Ala Thr Leu Glu
            435                 440                 445

Thr Lys Gln Pro Arg Gln Tyr Phe Ile Gly Val Leu Asp Ile Ala Gly
        450                 455                 460

Phe Glu Ile Phe Asp Phe Asn Ser Phe Glu Gln Leu Cys Ile Asn Phe
465                 470                 475                 480

Thr Asn Glu Lys Leu Gln Gln Phe Phe Asn His His Met Phe Val Leu
                485                 490                 495

Glu Gln Glu Glu Tyr Lys Lys Glu Gly Ile Glu Trp Thr Phe Ile Asp
            500                 505                 510

Phe Gly Met Asp Leu Gln Ala Cys Ile Asp Leu Ile Glu Lys Pro Met
        515                 520                 525

Gly Ile Met Ser Ile Leu Glu Glu Glu Cys Met Phe Pro Lys Ala Thr
530                 535                 540

Asp Met Thr Phe Lys Ala Lys Leu Phe Asp Asn His Leu Gly Lys Ser
545                 550                 555                 560

Ala Asn Phe Gln Lys Pro Arg Asn Ile Lys Gly Lys Pro Glu Ala His
                565                 570                 575

Phe Ser Leu Ile His Tyr Ala Gly Ile Val Asp Tyr Asn Ile Ile Gly
            580                 585                 590

Trp Leu Gln Lys Asn Lys Asp Pro Leu Asn Glu Thr Val Val Gly Leu
        595                 600                 605

Tyr Gln Lys Ser Ser Leu Lys Leu Leu Ser Thr Leu Phe Ala Asn Tyr
        610                 615                 620

Ala Gly Ala Asp Ala Pro Ile Glu Lys Gly Lys Gly Lys Ala Lys Lys
625                 630                 635                 640

Gly Ser Ser Phe Gln Thr Val Ser Ala Leu His Arg Glu Asn Leu Asn
                645                 650                 655

Lys Leu Met Thr Asn Leu Arg Ser Thr His Pro His Phe Val Arg Cys
            660                 665                 670

Ile Ile Pro Asn Glu Thr Lys Ser Pro Gly Val Met Asp Asn Pro Leu
        675                 680                 685

Val Met His Gln Leu Arg Cys Asn Gly Val Leu Glu Gly Ile Arg Ile
690                 695                 700

Cys Arg Lys Gly Phe Pro Asn Arg Ile Leu Tyr Gly Asp Phe Arg Gln
705                 710                 715                 720

Arg Tyr Arg Ile Leu Asn Pro Ala Ala Ile Pro Glu Gly Gln Phe Ile
                725                 730                 735

Asp Ser Arg Lys Gly Ala Glu Lys Leu Leu Ser Ser Leu Asp Ile Asp
            740                 745                 750

His Asn Gln Tyr Lys Phe Gly His Thr Lys Val Phe Phe Lys Ala Gly
        755                 760                 765

Leu Leu Gly Leu Leu Glu Glu Met Arg Asp Glu Arg Leu Ser Arg Ile
        770                 775                 780

Ile Thr Arg Ile Gln Ala Gln Ser Arg Gly Val Leu Ala Arg Met Glu
785                 790                 795                 800

Tyr Lys Lys Leu Leu Glu Arg Arg Asp Ser Leu Leu Val Ile Gln Trp
                805                 810                 815

Asn Ile Arg Ala Phe Met Gly Val Lys Asn Trp Pro Trp Met Lys Leu
            820                 825                 830

```
Tyr Phe Lys Ile Lys Pro Leu Leu Lys Ser Ala Glu Arg Glu Lys Glu
            835                 840                 845
Met Ala Ser Met Lys Glu Glu Phe Thr Arg Leu Lys Glu Ala Leu Glu
850                 855                 860
Lys Ser Glu Ala Arg Arg Lys Glu Leu Glu Glu Lys Met Val Ser Leu
865                 870                 875                 880
Leu Gln Glu Lys Asn Asp Leu Gln Leu Gln Val Gln Ala Glu Gln Asp
                885                 890                 895
Asn Leu Ala Asp Ala Glu Glu Arg Cys Asp Gln Leu Ile Lys Asn Lys
            900                 905                 910
Ile Gln Leu Glu Ala Lys Val Lys Glu Met Asn Glu Arg Leu Glu Asp
        915                 920                 925
Glu Glu Glu Met Asn Ala Glu Leu Thr Ala Lys Lys Arg Lys Leu Glu
    930                 935                 940
Asp Glu Cys Ser Glu Leu Lys Arg Asp Ile Asp Asp Leu Glu Leu Thr
945                 950                 955                 960
Leu Ala Lys Val Glu Lys Glu Lys His Ala Thr Glu Asn Lys Val Lys
                965                 970                 975
Asn Leu Thr Glu Glu Met Ala Gly Leu Asp Glu Ile Ile Ala Lys Leu
            980                 985                 990
Thr Lys Glu Lys Lys Ala Leu Gln  Glu Ala His Gln Gln  Ala Leu Asp
        995                 1000                 1005
Asp Leu  Gln Ala Glu Glu Asp  Lys Val Asn Thr Leu  Thr Lys Ala
    1010                 1015                 1020
Lys Val  Lys Leu Glu Gln Gln  Val Asp Asp Leu Glu  Gly Ser Leu
    1025                 1030                 1035
Glu Gln  Glu Lys Lys Val Arg  Met Asp Leu Glu Arg  Ala Lys Arg
    1040                 1045                 1050
Lys Leu  Glu Gly Asp Leu Lys  Leu Thr Gln Glu Ser  Ile Met Asp
    1055                 1060                 1065
Leu Glu  Asn Asp Lys Gln Gln  Leu Asp Glu Arg Leu  Lys Lys Lys
    1070                 1075                 1080
Asp Phe  Glu Leu Asn Ala Leu  Asn Ala Arg Ile Glu  Asp Glu Gln
    1085                 1090                 1095
Ala Leu  Gly Ser Gln Leu Gln  Lys Lys Leu Lys Glu  Leu Gln Ala
    1100                 1105                 1110
Arg Ile  Glu Glu Leu Glu Glu  Glu Leu Glu Ser Glu  Arg Thr Ala
    1115                 1120                 1125
Arg Ala  Lys Val Glu Lys Leu  Arg Ser Asp Leu Ser  Arg Glu Leu
    1130                 1135                 1140
Glu Glu  Ile Ser Glu Arg Leu  Glu Glu Ala Gly Gly  Ala Thr Ser
    1145                 1150                 1155
Val Gln  Ile Glu Met Asn Lys  Lys Arg Glu Ala Glu  Phe Gln Lys
    1160                 1165                 1170
Met Arg  Arg Asp Leu Glu Glu  Ala Thr Leu Gln His  Glu Ala Thr
    1175                 1180                 1185
Ala Ala  Ala Leu Arg Lys Lys  His Ala Asp Ser Val  Ala Glu Leu
    1190                 1195                 1200
Gly Glu  Gln Ile Asp Asn Leu  Gln Arg Val Lys Gln  Lys Leu Glu
    1205                 1210                 1215
Lys Glu  Lys Ser Glu Phe Lys  Leu Glu Leu Asp Asp  Val Thr Ser
    1220                 1225                 1230
Asn Met  Glu Gln Ile Ile Lys  Ala Lys Ala Asn Leu  Glu Lys Met
```

-continued

```
            1235                1240                1245
Cys Arg Thr Leu Glu Asp Gln Met Asn Glu His Arg Ser Lys Ala
    1250                1255                1260
Glu Glu Thr Gln Arg Ser Val Asn Asp Leu Thr Ser Gln Arg Ala
    1265                1270                1275
Lys Leu Gln Thr Glu Asn Gly Glu Leu Ser Arg Gln Leu Asp Glu
    1280                1285                1290
Lys Glu Ala Leu Ile Ser Gln Leu Thr Arg Gly Lys Leu Thr Tyr
    1295                1300                1305
Thr Gln Gln Leu Glu Asp Leu Lys Arg Gln Leu Glu Glu Glu Val
    1310                1315                1320
Lys Ala Lys Asn Ala Leu Ala His Ala Leu Gln Ser Ala Arg His
    1325                1330                1335
Asp Cys Asp Leu Leu Arg Glu Gln Tyr Glu Glu Glu Thr Glu Ala
    1340                1345                1350
Lys Ala Glu Leu Gln Arg Val Leu Ser Lys Ala Asn Ser Glu Val
    1355                1360                1365
Ala Gln Trp Arg Thr Lys Tyr Glu Thr Asp Ala Ile Gln Arg Thr
    1370                1375                1380
Glu Glu Leu Glu Glu Ala Lys Lys Lys Leu Ala Gln Arg Leu Gln
    1385                1390                1395
Glu Ala Glu Glu Ala Val Glu Ala Val Asn Ala Lys Cys Ser Ser
    1400                1405                1410
Leu Glu Lys Thr Lys His Arg Leu Gln Asn Glu Ile Glu Asp Leu
    1415                1420                1425
Met Val Asp Val Glu Arg Ser Asn Ala Ala Ala Ala Leu Asp
    1430                1435                1440
Lys Lys Gln Arg Asn Phe Asp Lys Ile Leu Ala Glu Trp Lys Gln
    1445                1450                1455
Lys Tyr Glu Glu Ser Gln Ser Glu Leu Glu Ser Ser Gln Lys Glu
    1460                1465                1470
Ala Arg Ser Leu Ser Thr Glu Leu Phe Lys Leu Lys Asn Ala Tyr
    1475                1480                1485
Glu Glu Ser Leu Glu His Leu Glu Thr Phe Lys Arg Glu Asn Lys
    1490                1495                1500
Asn Leu Gln Glu Glu Ile Ser Asp Leu Thr Glu Gln Leu Gly Ser
    1505                1510                1515
Ser Gly Lys Thr Ile His Glu Leu Glu Lys Val Arg Lys Gln Leu
    1520                1525                1530
Glu Ala Glu Lys Met Glu Leu Gln Ser Ala Leu Glu Glu Ala Glu
    1535                1540                1545
Ala Ser Leu Glu His Glu Glu Gly Lys Ile Leu Arg Ala Gln Leu
    1550                1555                1560
Glu Phe Asn Gln Ile Lys Ala Glu Ile Glu Arg Lys Leu Ala Glu
    1565                1570                1575
Lys Asp Glu Glu Met Glu Gln Ala Lys Arg Asn His Leu Arg Val
    1580                1585                1590
Val Asp Ser Leu Gln Thr Ser Leu Asp Ala Glu Thr Arg Ser Arg
    1595                1600                1605
Asn Glu Ala Leu Arg Val Lys Lys Lys Met Glu Gly Asp Leu Asn
    1610                1615                1620
Glu Met Glu Ile Gln Leu Ser His Ala Asn Arg Met Ala Ala Glu
    1625                1630                1635
```

```
Ala Gln Lys Gln Val Lys Ser Leu Gln Ser Leu Leu Lys Asp Thr
    1640            1645                1650

Gln Ile Gln Leu Asp Asp Ala Val Arg Ala Asn Asp Asp Leu Lys
    1655            1660                1665

Glu Asn Ile Ala Ile Val Glu Arg Arg Asn Asn Leu Leu Gln Ala
    1670            1675                1680

Glu Leu Glu Glu Leu Arg Ala Val Val Glu Gln Thr Glu Arg Ser
    1685            1690                1695

Arg Lys Leu Ala Glu Gln Glu Leu Ile Glu Thr Ser Glu Arg Val
    1700            1705                1710

Gln Leu Leu His Ser Gln Asn Thr Ser Leu Ile Asn Gln Lys Lys
    1715            1720                1725

Lys Met Asp Ala Asp Leu Ser Gln Leu Gln Thr Glu Val Glu Glu
    1730            1735                1740

Ala Val Gln Glu Cys Arg Asn Ala Glu Glu Lys Ala Lys Lys Ala
    1745            1750                1755

Ile Thr Asp Ala Ala Met Met Ala Glu Glu Leu Lys Lys Glu Gln
    1760            1765                1770

Asp Thr Ser Ala His Leu Glu Arg Met Lys Lys Asn Met Glu Gln
    1775            1780                1785

Thr Ile Lys Asp Leu Gln His Arg Leu Asp Glu Ala Glu Gln Ile
    1790            1795                1800

Ala Leu Lys Gly Gly Lys Lys Gln Leu Gln Lys Leu Glu Ala Arg
    1805            1810                1815

Val Arg Glu Leu Glu Asn Glu Leu Glu Ala Glu Gln Lys Arg Asn
    1820            1825                1830

Ala Glu Ser Val Lys Gly Met Arg Lys Ser Glu Arg Arg Ile Lys
    1835            1840                1845

Glu Leu Thr Tyr Gln Thr Glu Glu Asp Arg Lys Asn Leu Leu Arg
    1850            1855                1860

Leu Gln Asp Leu Val Asp Lys Leu Gln Leu Lys Val Lys Ala Tyr
    1865            1870                1875

Lys Arg Gln Ala Glu Glu Ala Glu Glu Gln Ala Asn Thr Asn Leu
    1880            1885                1890

Ser Lys Phe Arg Lys Val Gln His Glu Leu Asp Glu Ala Glu Glu
    1895            1900                1905

Arg Ala Asp Ile Ala Glu Ser Gln Val Asn Lys Leu Arg Ala Lys
    1910            1915                1920

Ser Arg Asp Ile Gly Thr Lys Gly Leu Asn Glu Glu
    1925            1930                1935

<210> SEQ ID NO 2
<211> LENGTH: 166
<212> TYPE: PRT
<213> ORGANISM: Homo sapiens

<400> SEQUENCE: 2

Met Ala Pro Lys Lys Ala Lys Lys Arg Ala Gly Gly Ala Asn Ser Asn
1               5                   10                  15

Val Phe Ser Met Phe Glu Gln Thr Gln Ile Gln Glu Phe Lys Glu Ala
                20                  25                  30

Phe Thr Ile Met Asp Gln Asn Arg Asp Gly Phe Ile Asp Lys Asn Asp
            35                  40                  45

Leu Arg Asp Thr Phe Ala Ala Leu Gly Arg Val Asn Val Lys Asn Glu
```

-continued

```
                50                  55                  60
Glu Ile Asp Glu Met Ile Lys Glu Ala Pro Gly Pro Ile Asn Phe Thr
65                  70                  75                  80

Val Phe Leu Thr Met Phe Gly Glu Lys Leu Lys Gly Ala Asp Pro Glu
                85                  90                  95

Glu Thr Ile Leu Asn Ala Phe Lys Val Phe Asp Pro Glu Gly Lys Gly
                100                 105                 110

Val Leu Lys Ala Asp Tyr Val Arg Glu Met Leu Thr Thr Gln Ala Glu
                115                 120                 125

Arg Phe Ser Lys Glu Val Asp Gln Met Phe Ala Ala Phe Pro Pro
                130                 135                 140

Asp Val Thr Gly Asn Leu Asp Tyr Lys Asn Leu Val His Ile Ile Thr
145                 150                 155                 160

His Gly Glu Glu Lys Asp
                165
```

The invention claimed is:

1. A method for producing a β myosin heavy chain in cardiac muscle cells differentiated from human induced pluripotent stem cells, the method comprising:
   (a) supplying a liquid culture medium containing the cardiac muscle cells onto a substrate comprising a first electrode, a second electrode and insulative fibers on the surface thereof to coat a surface of the first electrode, a surface of the second electrode, and a region between the first electrode and the second electrode with the cardiac muscle cells;
   wherein
   at least a part of the insulative fibers is located between the first electrode and the second electrode in a top view of the substrate; and
   an angle formed between each of not less than 90% of the insulative fibers and an imaginary straight line which passes through both the first electrode and the second electrode is not more than ±20 degrees in the top view;
   (b) leaving the substrate at rest;
   (c) cultivating the cardiac muscle cells, while a pulse electric current is applied to the cardiac muscle cells through the first electrode and the second electrode; and
   (d) obtaining the β myosin heavy chain produced in the cultivated cardiac muscle cells.

2. The method according to claim 1, wherein in the step (b), the substrate is left at rest until the cardiac muscle cells adhere on the surface of the substrate or the insulative fibers.

3. The method according to claim 1, wherein a reference electrode is in contact with the liquid culture medium.

4. The method according to claim 3, wherein the reference electrode is grounded.

5. The method according to claim 3, wherein the substrate comprises the reference electrode on the surface thereof.

6. The method according to claim 3, wherein the liquid culture medium includes the reference electrode.

* * * * *